US009554929B2

(12) United States Patent
Arbefeuille et al.

(10) Patent No.: US 9,554,929 B2
(45) Date of Patent: Jan. 31, 2017

(54) VASCULAR PROSTHETIC DELIVERY DEVICE AND METHOD OF USE

(71) Applicant: Bolton Medical, Inc., Sunrise, FL (US)

(72) Inventors: Samuel Arbefeuille, Sunrise, FL (US); Fletcher Christian, Sunrise, FL (US); John C. Canning, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 161 days.

(21) Appl. No.: 14/639,280

(22) Filed: Mar. 5, 2015

(65) Prior Publication Data

US 2015/0173922 A1 Jun. 25, 2015

Related U.S. Application Data

(62) Division of application No. 13/829,508, filed on Mar. 14, 2013, now Pat. No. 8,998,970.

(Continued)

(51) Int. Cl.
*A61F 2/06* (2013.01)
*A61F 2/95* (2013.01)
*A61F 2/966* (2013.01)

(52) U.S. Cl.
CPC .............. *A61F 2/95* (2013.01); *A61F 2/966* (2013.01); *A61F 2002/9517* (2013.01); *A61F 2002/9665* (2013.01)

(58) Field of Classification Search
CPC .............. A61F 2002/9517; A61F 2/95; A61F 2002/9665; A61F 2/966

(Continued)

(56) References Cited

U.S. PATENT DOCUMENTS 3,416,531 A 12/1968 Edwards
3,485,234 A 12/1969 Stevens
(Continued)

FOREIGN PATENT DOCUMENTS

CN 2451136 Y 10/2001
DE 197 53 123 A1 8/1999
(Continued)

OTHER PUBLICATIONS

Notification of Transmittal of the International Search Report and the Written Opinion of the International Searching Authority, or the Declaration in re PCT/US2013/031702, Titled: "Vascular Prosthetic Delivery Device and Method of Use", Date of mailing Jul. 2, 2013.

(Continued)

*Primary Examiner* — Katherine M Shi
(74) *Attorney, Agent, or Firm* — Hamilton, Brook, Smith & Reynolds, P.C.

(57) ABSTRACT

Methods for delivering a vascular prosthesis to a treatment site of a subject include advancing the vascular prosthesis, rotating a proximal handle in a first direction about a handle body, shifting the position of a first locking component securing the proximal handle to the push rod from a first position to a second position, rotating the proximal handle in a second direction, releasing the proximal end of the prosthesis from the apex delivery device, shifting the second locking component to disengage the push rod from the handle body; and withdrawing the push rod and the guidewire catheter from within the prosthesis, thereby delivering the vascular prosthesis to the treatment site.

13 Claims, 27 Drawing Sheets

Related U.S. Application Data

(60) Provisional application No. 61/623,235, filed on Apr. 12, 2012.

(58) Field of Classification Search
USPC .............. 623/1.11, 1.12, 1.23; 606/194, 200
See application file for complete search history.

(56) References Cited

U.S. PATENT DOCUMENTS

| | | |
|---|---|---|
| 3,502,069 A | 3/1970 | Silverman |
| 3,868,956 A | 3/1975 | Alfidi |
| 4,351,333 A | 9/1982 | Lazarus |
| 4,425,919 A | 1/1984 | Alston |
| 4,487,808 A | 12/1984 | Lambert |
| 4,515,593 A | 5/1985 | Norton |
| 4,516,972 A | 5/1985 | Samson |
| 4,534,363 A | 8/1985 | Gold |
| 4,572,186 A | 2/1986 | Gould |
| 4,580,568 A | 4/1986 | Gianturco |
| 4,634,432 A | 1/1987 | Kocak |
| 4,655,771 A | 4/1987 | Wallsten |
| 4,665,906 A | 5/1987 | Jervis |
| 4,665,918 A | 5/1987 | Garza et al. |
| 4,705,511 A | 11/1987 | Kocak |
| 4,787,899 A | 11/1988 | Lazarus |
| 4,817,613 A | 4/1989 | Jaraczewski |
| 4,990,151 A | 2/1991 | Wallsten et al. |
| 5,019,057 A | 5/1991 | Truckai |
| 5,041,126 A | 8/1991 | Gianturco |
| 5,057,092 A | 10/1991 | Webster |
| 5,067,957 A | 11/1991 | Jervis |
| 5,104,399 A | 4/1992 | Lazarus |
| 5,154,701 A | 10/1992 | Cheer et al. |
| 5,158,543 A | 10/1992 | Lazarus |
| 5,176,652 A | 1/1993 | Littrell |
| 5,176,660 A | 1/1993 | Truckai |
| 5,201,757 A | 4/1993 | Heyn et al. |
| 5,254,105 A | 10/1993 | Haaga |
| 5,282,824 A | 2/1994 | Gianturco |
| 5,290,295 A | 3/1994 | Querals et al. |
| 5,292,331 A | 3/1994 | Boneau |
| 5,306,263 A | 4/1994 | Voda |
| 5,324,306 A | 6/1994 | Makower et al. |
| 5,334,168 A | 8/1994 | Hemmer |
| 5,338,295 A | 8/1994 | Cornelius |
| 5,342,384 A | 8/1994 | Sugarbaker |
| 5,358,493 A | 10/1994 | Schweich |
| 5,380,304 A | 1/1995 | Parker |
| 5,387,235 A | 2/1995 | Chuter |
| 5,397,345 A | 3/1995 | Lazarus |
| 5,405,377 A | 4/1995 | Cragg |
| 5,415,664 A | 5/1995 | Pinchuk |
| 5,433,723 A | 7/1995 | Lindenberg et al. |
| 5,456,713 A | 10/1995 | Chuter |
| 5,458,615 A | 10/1995 | Klemm et al. |
| 5,464,449 A | 11/1995 | Ryan et al. |
| 5,474,563 A | 12/1995 | Myler et al. |
| 5,480,423 A | 1/1996 | Ravenscroft et al. |
| 5,489,295 A | 2/1996 | Piplani et al. |
| 5,507,771 A | 4/1996 | Gianturco |
| 5,522,881 A | 6/1996 | Lentz |
| 5,522,882 A | 6/1996 | Gaterud et al. |
| 5,531,715 A | 7/1996 | Engelson |
| 5,533,987 A | 7/1996 | Pray |
| 5,534,007 A | 7/1996 | St. Germain et al. |
| 5,540,712 A | 7/1996 | Kleshinski et al. |
| 5,545,210 A | 8/1996 | Hess et al. |
| 5,549,565 A | 8/1996 | Ryan et al. |
| 5,562,726 A | 10/1996 | Chuter |
| 5,562,728 A | 10/1996 | Lazarus et al. |
| 5,569,218 A | 10/1996 | Berg |
| 5,571,135 A | 11/1996 | Fraser et al. |
| 5,575,816 A | 11/1996 | Rudnick et al. |
| 5,575,817 A | 11/1996 | Martin |
| 5,582,614 A | 12/1996 | Feingold |
| 5,591,195 A | 1/1997 | Taheri et al. |
| 5,597,378 A | 1/1997 | Jervis |
| 5,601,568 A | 2/1997 | Chevillon et al. |
| 5,607,442 A | 3/1997 | Fischell et al. |
| 5,609,625 A | 3/1997 | Piplani et al. |
| 5,609,627 A | 3/1997 | Goicoechea et al. |
| 5,613,974 A | 3/1997 | Andreas et al. |
| 5,618,270 A | 4/1997 | Orejola |
| 5,628,754 A | 5/1997 | Shevlin |
| 5,628,783 A | 5/1997 | Quiachon et al. |
| 5,632,763 A | 5/1997 | Glastra |
| 5,639,278 A | 6/1997 | Dereume et al. |
| 5,658,263 A | 8/1997 | Dang |
| 5,662,675 A | 9/1997 | Polanskyj Stockert et al. |
| 5,662,700 A | 9/1997 | Lazarus |
| 5,674,208 A | 10/1997 | Berg |
| 5,676,696 A | 10/1997 | Marcade |
| 5,683,449 A | 11/1997 | Marcade |
| 5,693,086 A | 12/1997 | Goicoechea et al. |
| 5,700,269 A | 12/1997 | Pinchuk et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,716,365 A | 2/1998 | Goicoechea et al. |
| 5,716,393 A | 2/1998 | Lindenberg et al. |
| 5,720,776 A | 2/1998 | Chuter et al. |
| 5,723,003 A | 3/1998 | Winston et al. |
| 5,730,733 A | 3/1998 | Mortier |
| 5,733,267 A | 3/1998 | Del Toro |
| 5,735,859 A | 4/1998 | Fischell et al. |
| 5,749,921 A | 5/1998 | Lenker et al. |
| 5,755,778 A | 5/1998 | Kleshinski |
| 5,776,142 A | 7/1998 | Gunderson |
| 5,782,811 A | 7/1998 | Samson |
| 5,782,904 A | 7/1998 | White et al. |
| 5,782,909 A | 7/1998 | Quiachon et al. |
| 5,788,707 A | 8/1998 | Del Toro et al. |
| 5,792,144 A | 8/1998 | Fischell et al. |
| 5,800,515 A | 9/1998 | Nadal et al. |
| 5,800,517 A | 9/1998 | Anderson et al. |
| 5,800,520 A | 9/1998 | Fogarty et al. |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,843,158 A | 12/1998 | Lenker et al. |
| 5,843,160 A | 12/1998 | Rhodes |
| 5,843,164 A | 12/1998 | Frantzen et al. |
| 5,843,167 A | 12/1998 | Dwyer et al. |
| 5,851,228 A | 12/1998 | Pinheiro |
| 5,860,998 A | 1/1999 | Robinson et al. |
| 5,871,536 A | 2/1999 | Lazarus |
| 5,891,110 A | 4/1999 | Larson |
| 5,891,114 A | 4/1999 | Chien |
| 5,893,868 A | 4/1999 | Hanson et al. |
| 5,899,892 A | 5/1999 | Mortier |
| 5,902,334 A | 5/1999 | Dwyer et al. |
| 5,904,713 A | 5/1999 | Leschinsky |
| 5,906,619 A | 5/1999 | Olson et al. |
| 5,910,101 A | 6/1999 | Andrews et al. |
| 5,911,715 A | 6/1999 | Berg |
| 5,916,263 A | 6/1999 | Goicoechea et al. |
| 5,938,696 A | 8/1999 | Goicoechea et al. |
| 5,944,726 A | 8/1999 | Blaeser et al. |
| 5,947,939 A | 9/1999 | Mortier |
| 5,951,495 A | 9/1999 | Berg |
| 5,954,651 A | 9/1999 | Berg |
| 5,957,949 A | 9/1999 | Leonhardt et al. |
| 5,961,511 A | 10/1999 | Mortier |
| 5,968,069 A | 10/1999 | Dusbabek et al. |
| 5,984,955 A | 11/1999 | Wisselink |
| 5,993,481 A | 11/1999 | Marcade et al. |
| 6,004,310 A | 12/1999 | Bardsley |
| 6,004,328 A | 12/1999 | Solar |
| 6,004,347 A | 12/1999 | McNamara et al. |
| 6,019,778 A | 2/2000 | Wilson et al. |

(56) References Cited

U.S. PATENT DOCUMENTS

| | | |
|---|---|---|
| 6,024,763 A | 2/2000 | Lenker et al. |
| 6,039,749 A | 3/2000 | Marin et al. |
| 6,039,758 A | 3/2000 | Quiachon et al. |
| 6,039,759 A | 3/2000 | Carpentier et al. |
| 6,045,557 A | 4/2000 | White et al. |
| 6,051,020 A | 4/2000 | Goicoechea et al. |
| 6,053,943 A | 4/2000 | Edwin et al. |
| 6,063,112 A | 5/2000 | Sgro |
| 6,071,307 A | 6/2000 | Rhee |
| 6,077,297 A | 6/2000 | Robinson et al. |
| 6,099,548 A | 8/2000 | Taheri |
| 6,099,558 A | 8/2000 | White et al. |
| 6,099,559 A | 8/2000 | Nolting |
| 6,110,191 A | 8/2000 | Dehdashtian et al. |
| 6,110,198 A | 8/2000 | Fogarty et al. |
| 6,117,167 A | 9/2000 | Goicoechea et al. |
| 6,120,480 A | 9/2000 | Zhang et al. |
| 6,123,723 A | 9/2000 | Konya et al. |
| 6,152,944 A | 11/2000 | Holman et al. |
| 6,165,163 A | 12/2000 | Chien |
| 6,165,213 A | 12/2000 | Goicoechea et al. |
| 6,168,616 B1 | 1/2001 | Brown, III |
| 6,168,623 B1 | 1/2001 | Fogarty et al. |
| 6,183,481 B1 | 2/2001 | Lee et al. |
| 6,183,505 B1 | 2/2001 | Mohn |
| 6,183,506 B1 | 2/2001 | Penn et al. |
| 6,193,705 B1 | 2/2001 | Mortier |
| 6,200,336 B1 | 3/2001 | Pavcnik et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,210,435 B1 | 4/2001 | Piplani et al. |
| 6,212,422 B1 | 4/2001 | Berg |
| 6,213,976 B1 | 4/2001 | Trerotola |
| 6,214,038 B1 | 4/2001 | Piplani et al. |
| 6,221,079 B1 | 4/2001 | Magovern et al. |
| 6,221,102 B1 | 4/2001 | Baker et al. |
| 6,224,609 B1 | 5/2001 | Ressemann et al. |
| 6,228,063 B1 | 5/2001 | Aboul-Hosn |
| 6,231,601 B1 | 5/2001 | Myers et al. |
| 6,238,430 B1 | 5/2001 | Klumb et al. |
| 6,245,052 B1 | 6/2001 | Orth et al. |
| 6,248,112 B1 | 6/2001 | Gambale et al. |
| 6,248,116 B1 | 6/2001 | Chevillon |
| 6,251,132 B1 | 6/2001 | Ravenscroft et al. |
| 6,254,609 B1 | 7/2001 | Vrba et al. |
| 6,267,775 B1 | 7/2001 | Clerc et al. |
| 6,270,521 B1 | 8/2001 | Fischell et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,287,315 B1 | 9/2001 | Wijeratne et al. |
| 6,302,906 B1 | 10/2001 | Goicoechea et al. |
| 6,302,907 B1 | 10/2001 | Hijlkema |
| 6,306,141 B1 | 10/2001 | Jervis |
| 6,312,458 B1 | 11/2001 | Golds |
| 6,319,275 B1 | 11/2001 | Lashinski et al. |
| 6,319,278 B1 | 11/2001 | Quinn |
| 6,322,585 B1 | 11/2001 | Khosravi et al. |
| 6,334,869 B1 | 1/2002 | Leonhardt et al. |
| 6,338,709 B1 | 1/2002 | Geoffrion et al. |
| 6,342,066 B1 | 1/2002 | Toro et al. |
| 6,344,044 B1 | 2/2002 | Fulkerson |
| 6,344,052 B1 | 2/2002 | Greenan et al. |
| 6,346,118 B1 | 2/2002 | Baker et al. |
| 6,350,278 B1 | 2/2002 | Lenker et al. |
| 6,355,056 B1 | 3/2002 | Pinheiro |
| 6,355,060 B1 | 3/2002 | Lenker et al. |
| 6,368,345 B1 | 4/2002 | Dehdashtian et al. |
| 6,375,675 B2 | 4/2002 | Dehdashtian et al. |
| 6,375,676 B1 | 4/2002 | Cox |
| 6,379,372 B1 | 4/2002 | Dehdashtian et al. |
| 6,389,946 B1 | 5/2002 | Frid et al. |
| 6,395,017 B1 | 5/2002 | Dwyer et al. |
| 6,395,022 B1 | 5/2002 | Piplani et al. |
| 6,402,781 B1 | 6/2002 | Langberg et al. |
| 6,416,490 B1 | 7/2002 | Ellis et al. |
| 6,416,542 B1 | 7/2002 | Marcade et al. |
| 6,419,686 B1 | 7/2002 | McLeod et al. |
| 6,425,898 B1 | 7/2002 | Wilson |
| 6,443,979 B1 | 9/2002 | Stalker et al. |
| 6,443,980 B1 | 9/2002 | Wang |
| 6,450,988 B1 | 9/2002 | Bradshaw |
| 6,451,053 B1 | 9/2002 | Dehdashtian et al. |
| 6,454,796 B1 | 9/2002 | Barkman et al. |
| 6,458,867 B1 | 10/2002 | Wang |
| 6,464,684 B1 | 10/2002 | Galdonik |
| 6,464,719 B2 | 10/2002 | Jayaraman |
| 6,464,721 B1 | 10/2002 | Marcade et al. |
| 6,478,818 B1 | 11/2002 | Taheri |
| 6,488,700 B2 | 12/2002 | Klumb et al. |
| 6,503,274 B1 | 1/2003 | Howanec, Jr. et al. |
| 6,505,066 B2 | 1/2003 | Berg |
| 6,514,282 B1 | 2/2003 | Inoue |
| 6,517,571 B1 | 2/2003 | Brauker et al. |
| 6,517,572 B2 | 2/2003 | Kugler et al. |
| 6,517,573 B1 | 2/2003 | Pollock et al. |
| 6,520,951 B1 | 2/2003 | Carrillo, Jr. et al. |
| 6,520,986 B2 | 2/2003 | Martin et al. |
| 6,524,335 B1 | 2/2003 | Hartley et al. |
| 6,524,336 B1 | 2/2003 | Papazolgou et al. |
| 6,533,753 B1 | 3/2003 | Haarstad et al. |
| 6,540,698 B1 | 4/2003 | Ishii |
| 6,540,778 B1 | 4/2003 | Piplani et al. |
| 6,551,350 B1 | 4/2003 | Thornton et al. |
| 6,562,022 B2 | 5/2003 | Hoste |
| 6,565,596 B1 | 5/2003 | White et al. |
| 6,565,597 B1 | 5/2003 | Fearnot et al. |
| 6,575,994 B1 | 6/2003 | Marin et al. |
| 6,576,007 B2 | 6/2003 | Dehdashtian et al. |
| 6,582,458 B1 | 6/2003 | White et al. |
| 6,582,460 B1 | 6/2003 | Cryer |
| 6,592,526 B1 | 7/2003 | Lenker |
| 6,613,073 B1 | 9/2003 | White et al. |
| 6,616,626 B2 | 9/2003 | Crank et al. |
| 6,620,126 B2 | 9/2003 | Unsworth et al. |
| 6,641,606 B2 | 11/2003 | Ouriel et al. |
| 6,652,571 B1 | 11/2003 | White et al. |
| 6,652,572 B2 | 11/2003 | Kugler et al. |
| 6,660,033 B1 | 12/2003 | Marcade et al. |
| 6,676,666 B2 | 1/2004 | Vrba et al. |
| 6,682,536 B2 | 1/2004 | Vardi et al. |
| 6,682,537 B2 | 1/2004 | Ouriel et al. |
| 6,682,557 B1 | 1/2004 | Quiachon et al. |
| 6,685,736 B1 | 2/2004 | White et al. |
| 6,689,152 B2 | 2/2004 | Balceta et al. |
| 6,689,158 B1 | 2/2004 | White et al. |
| 6,692,458 B2 | 2/2004 | Forman et al. |
| 6,692,483 B2 | 2/2004 | Vardi et al. |
| 6,692,512 B2 | 2/2004 | Jang |
| 6,695,875 B2 | 2/2004 | Stelter et al. |
| 6,706,033 B1 | 3/2004 | Martinez et al. |
| 6,726,712 B1 | 4/2004 | Raeder-Devens |
| 6,733,519 B2 | 5/2004 | Lashinski et al. |
| 6,733,523 B2 | 5/2004 | Shaolian et al. |
| 6,755,856 B2 | 6/2004 | Seibold et al. |
| 6,761,731 B2 | 7/2004 | Majercak |
| 6,790,222 B2 | 9/2004 | Kugler et al. |
| 6,802,860 B2 | 10/2004 | Cosgrove et al. |
| 6,808,529 B2 | 10/2004 | Fulkerson |
| 6,811,559 B2 | 11/2004 | Thornton |
| 6,814,748 B1 | 11/2004 | Baker et al. |
| 6,821,291 B2 | 11/2004 | Neisz et al. |
| 6,827,710 B1 | 12/2004 | Mooney et al. |
| 6,827,711 B2 | 12/2004 | Sunseri |
| 6,830,575 B2 | 12/2004 | Stenzel et al. |
| 6,843,803 B2 | 1/2005 | Ryan et al. |
| 6,849,084 B2 | 2/2005 | Rabkin et al. |
| 6,849,088 B2 | 2/2005 | Dehdashtian et al. |
| 6,858,034 B1 | 2/2005 | Hijlkema et al. |
| 6,859,986 B2 | 3/2005 | Jackson |
| 6,860,901 B1 | 3/2005 | Baker et al. |
| 6,863,668 B2 | 3/2005 | Gillespie et al. |
| 6,866,660 B2 | 3/2005 | Garabedian et al. |

(56) References Cited

U.S. PATENT DOCUMENTS

| | | | |
|---|---|---|---|
| 6,871,085 B2 | 3/2005 | Sommer | |
| 6,884,260 B2 | 4/2005 | Kugler et al. | |
| 6,890,348 B2 | 5/2005 | Sydney et al. | |
| 6,911,039 B2 | 6/2005 | Shiu et al. | |
| 6,916,335 B2 | 7/2005 | Kanji | |
| 6,918,925 B2 | 7/2005 | Tehrani | |
| 6,932,829 B2 | 8/2005 | Majercak | |
| 6,938,646 B2 | 9/2005 | Litton | |
| 6,939,371 B2 | 9/2005 | Kugler et al. | |
| 6,945,989 B1 | 9/2005 | Betelia et al. | |
| 6,945,990 B2 | 9/2005 | Greenan | |
| 6,964,679 B1 | 11/2005 | Marcade et al. | |
| 6,989,024 B2 | 1/2006 | Hebert et al. | |
| 6,994,722 B2 | 2/2006 | DiCarlo | |
| 7,001,420 B2 | 2/2006 | Speck et al. | |
| 7,011,647 B2 | 3/2006 | Purdy et al. | |
| 7,014,653 B2 | 3/2006 | Ouriel | |
| 7,025,773 B2 | 4/2006 | Gittings et al. | |
| 7,052,511 B2 * | 5/2006 | Weldon | A61F 2/95 606/194 |
| 7,070,582 B2 | 7/2006 | Freyman et al. | |
| 7,105,016 B2 | 9/2006 | Shiu et al. | |
| 7,112,217 B1 | 9/2006 | Kugler et al. | |
| 7,115,134 B2 | 10/2006 | Chambers | |
| 7,125,419 B2 | 10/2006 | Sequin et al. | |
| 7,147,657 B2 | 12/2006 | Chiang et al. | |
| 7,147,660 B2 | 12/2006 | Chobotov et al. | |
| 7,160,318 B2 | 1/2007 | Greenberg et al. | |
| 7,163,552 B2 | 1/2007 | Diaz | |
| 7,166,125 B1 | 1/2007 | Baker et al. | |
| 7,169,170 B2 | 1/2007 | Widenhouse | |
| 7,195,639 B2 | 3/2007 | Quiachon et al. | |
| 7,225,518 B2 | 6/2007 | Eidenschink et al. | |
| 7,238,197 B2 | 7/2007 | Sequin et al. | |
| 7,264,632 B2 | 9/2007 | Wright et al. | |
| 7,294,147 B2 | 11/2007 | Hartley | |
| 7,351,256 B2 | 4/2008 | Hojeibane et al. | |
| 7,708,771 B2 | 5/2010 | Chuter et al. | |
| 7,717,950 B2 | 5/2010 | Greenan | |
| 7,722,663 B1 | 5/2010 | Austin | |
| 7,763,063 B2 | 7/2010 | Arbefeuille et al. | |
| 7,766,962 B1 | 8/2010 | Quinn | |
| 7,837,724 B2 | 11/2010 | Keeble et al. | |
| 8,043,354 B2 | 10/2011 | Greenberg et al. | |
| 8,062,345 B2 | 11/2011 | Ouellette et al. | |
| 8,062,349 B2 | 11/2011 | Moore et al. | |
| 8,070,790 B2 | 12/2011 | Berra et al. | |
| 8,292,943 B2 | 10/2012 | Berra et al. | |
| 8,308,790 B2 | 11/2012 | Arbefeuille et al. | |
| 8,449,595 B2 | 5/2013 | Ouellette et al. | |
| 8,500,792 B2 | 8/2013 | Berra | |
| 8,579,963 B2 | 11/2013 | Tabor | |
| 8,636,788 B2 | 1/2014 | Arbefeuille et al. | |
| 8,672,992 B2 | 3/2014 | Orr | |
| 8,702,787 B2 | 4/2014 | Arbefeuille | |
| 8,734,501 B2 | 5/2014 | Hartley et al. | |
| 8,740,963 B2 | 6/2014 | Arbefeuille et al. | |
| 8,998,970 B2 | 4/2015 | Arbefeuille et al. | |
| 9,101,506 B2 | 8/2015 | Arbefeuille et al. | |
| 9,173,755 B2 | 11/2015 | Berra et al. | |
| 9,198,786 B2 | 12/2015 | Moore et al. | |
| 9,220,617 B2 | 12/2015 | Berra | |
| 9,320,631 B2 | 4/2016 | Moore et al. | |
| 9,333,104 B2 | 5/2016 | Ouellette et al. | |
| 9,364,314 B2 | 6/2016 | Berra et al. | |
| 2001/0000801 A1 | 5/2001 | Miller et al. | |
| 2001/0001833 A1 | 5/2001 | Ravenscroft et al. | |
| 2001/0034549 A1 | 10/2001 | Bartholf et al. | |
| 2001/0049547 A1 | 12/2001 | Moore | |
| 2002/0007193 A1 | 1/2002 | Tanner et al. | |
| 2002/0013617 A1 | 1/2002 | Matsutani et al. | |
| 2002/0016597 A1 | 2/2002 | Dwyer et al. | |
| 2002/0016627 A1 | 2/2002 | Golds | |
| 2002/0035394 A1 | 3/2002 | Fierens | |
| 2002/0045929 A1 | 4/2002 | Diaz | |
| 2002/0052643 A1 | 5/2002 | Wholey et al. |
| 2002/0052660 A1 | 5/2002 | Greenhalgh |
| 2002/0072755 A1 | 6/2002 | Bigus et al. |
| 2002/0082523 A1 | 6/2002 | Kinsella et al. |
| 2002/0082674 A1 | 6/2002 | Anson et al. |
| 2002/0091439 A1 | 7/2002 | Baker et al. |
| 2002/0095140 A1 | 7/2002 | Lootz et al. |
| 2002/0107561 A1 | 8/2002 | Pinheiro |
| 2002/0108621 A1 | 8/2002 | Berg et al. |
| 2002/0138133 A1 | 9/2002 | Lenz et al. |
| 2002/0156518 A1 | 10/2002 | Tehrani |
| 2002/0156522 A1 | 10/2002 | Ivancev et al. |
| 2002/0161424 A1 | 10/2002 | Rapacki et al. |
| 2002/0188344 A1 | 12/2002 | Bolea et al. |
| 2002/0198587 A1 | 12/2002 | Greenberg et al. |
| 2003/0028237 A1 | 2/2003 | Sullivan et al. |
| 2003/0074049 A1 | 4/2003 | Hoganson et al. |
| 2003/0083734 A1 | 5/2003 | Friedrich et al. |
| 2003/0088305 A1 | 5/2003 | Van Schie et al. |
| 2003/0114910 A1 | 6/2003 | Juhani Laakso et al. |
| 2003/0120263 A1 | 6/2003 | Ouriel et al. |
| 2003/0135259 A1 | 7/2003 | Simso |
| 2003/0135269 A1 | 7/2003 | Swanstrom |
| 2003/0139803 A1 | 7/2003 | Sequin et al. |
| 2003/0163156 A1 | 8/2003 | Hebert et al. |
| 2003/0163193 A1 | 8/2003 | Widenhouse |
| 2003/0176911 A1 | 9/2003 | Iancea et al. |
| 2003/0195614 A1 | 10/2003 | Ryan et al. |
| 2003/0199966 A1 | 10/2003 | Shiu et al. |
| 2003/0199967 A1 | 10/2003 | Hartley et al. |
| 2003/0212431 A1 | 11/2003 | Brady et al. |
| 2003/0220682 A1 | 11/2003 | Kujawski |
| 2003/0236564 A1 | 12/2003 | Majercak |
| 2003/0236565 A1 | 12/2003 | DiMatteo et al. |
| 2004/0073284 A1 | 4/2004 | Bates et al. |
| 2004/0073289 A1 | 4/2004 | Hartley |
| 2004/0093063 A1 | 5/2004 | Wright et al. |
| 2004/0098084 A1 | 5/2004 | Hartley et al. |
| 2004/0106974 A1 | 6/2004 | Greenberg et al. |
| 2004/0117003 A1 | 6/2004 | Ouriel et al. |
| 2004/0148007 A1 | 7/2004 | Jackson et al. |
| 2004/0148009 A1 | 7/2004 | Buzzard et al. |
| 2004/0193141 A1 | 9/2004 | Leopold et al. |
| 2004/0193244 A1 | 9/2004 | Hartley et al. |
| 2004/0193245 A1 | 9/2004 | Deem et al. |
| 2004/0193252 A1 | 9/2004 | Perez |
| 2004/0199240 A1 | 10/2004 | Dorn |
| 2004/0230286 A1 | 11/2004 | Moore et al. |
| 2004/0236403 A1 | 11/2004 | Leonhardt et al. |
| 2004/0236407 A1 | 11/2004 | Fierens et al. |
| 2004/0267281 A1 | 12/2004 | Harari et al. |
| 2005/0021125 A1 | 1/2005 | Stack et al. |
| 2005/0027305 A1 | 2/2005 | Shiu et al. |
| 2005/0033406 A1 | 2/2005 | Barnhart et al. |
| 2005/0038495 A1 | 2/2005 | Greenan |
| 2005/0049667 A1 | 3/2005 | Arbefeuille et al. |
| 2005/0049674 A1 | 3/2005 | Berra et al. |
| 2005/0080476 A1 | 4/2005 | Gunderson et al. |
| 2005/0080477 A1 | 4/2005 | Sydney et al. |
| 2005/0096726 A1 | 5/2005 | Sequin et al. |
| 2005/0107862 A1 | 5/2005 | Ohlenschlaeger |
| 2005/0149166 A1 | 7/2005 | Schaeffer et al. |
| 2005/0159803 A1 | 7/2005 | Lad et al. |
| 2005/0159804 A1 | 7/2005 | Lad et al. |
| 2005/0171597 A1 | 8/2005 | Boatman et al. |
| 2005/0171598 A1 | 8/2005 | Schaeffer |
| 2005/0177222 A1 | 8/2005 | Mead |
| 2005/0183259 A1 | 8/2005 | Eidenschink et al. |
| 2005/0192659 A1 | 9/2005 | Dahl et al. |
| 2005/0222668 A1 | 10/2005 | Schaeffer et al. |
| 2005/0283223 A1 | 12/2005 | Greenan |
| 2005/0288764 A1 | 12/2005 | Snow et al. |
| 2006/0004433 A1 | 1/2006 | Greenberg et al. |
| 2006/0020319 A1 | 1/2006 | Kim et al. |
| 2006/0020320 A1 | 1/2006 | Shaolian et al. |
| 2006/0058864 A1 | 3/2006 | Schaeffer et al. |
| 2006/0127439 A1 | 6/2006 | Mattes et al. |
| 2006/0129169 A1 | 6/2006 | Fogarty et al. |
| 2006/0129224 A1 | 6/2006 | Arbefeuille et al. |

(56) References Cited

U.S. PATENT DOCUMENTS

| | | |
|---|---|---|
| 2006/0135961 A1 | 6/2006 | Rosenman et al. |
| 2006/0178726 A1 | 8/2006 | Douglas |
| 2006/0178733 A1 | 8/2006 | Pinchuk et al. |
| 2006/0188408 A1 | 8/2006 | Arbefeuille et al. |
| 2006/0195172 A1 | 8/2006 | Luo et al. |
| 2006/0200110 A1 | 9/2006 | Lentz et al. |
| 2006/0212105 A1 | 9/2006 | Dorn et al. |
| 2006/0265047 A1 | 11/2006 | Dorn |
| 2006/0276872 A1 | 12/2006 | Arbefeuille et al. |
| 2006/0282150 A1 | 12/2006 | Olson et al. |
| 2007/0021822 A1 | 1/2007 | Boatman |
| 2007/0048348 A1 | 3/2007 | Atanasoska et al. |
| 2007/0053952 A1 | 3/2007 | Chen et al. |
| 2007/0055338 A1 | 3/2007 | Dorn |
| 2007/0055340 A1 | 3/2007 | Pryor |
| 2007/0055341 A1 | 3/2007 | Edoga et al. |
| 2007/0055345 A1 | 3/2007 | Arbefeuille |
| 2007/0055347 A1 | 3/2007 | Arbefeuille |
| 2007/0083252 A1 | 4/2007 | McDonald |
| 2007/0100422 A1 | 5/2007 | Shumer et al. |
| 2007/0100425 A1 | 5/2007 | Sequin et al. |
| 2007/0123972 A1 | 5/2007 | Greenberg et al. |
| 2007/0135818 A1 | 6/2007 | Moore et al. |
| 2007/0135889 A1 | 6/2007 | Moore et al. |
| 2007/0142894 A1 | 6/2007 | Moore et al. |
| 2007/0156228 A1 | 7/2007 | Majercak et al. |
| 2007/0162109 A1 | 7/2007 | Davila et al. |
| 2007/0163668 A1 | 7/2007 | Arbefeuille et al. |
| 2007/0168014 A1 | 7/2007 | Jimenez et al. |
| 2007/0173929 A1 | 7/2007 | Boucher et al. |
| 2007/0179592 A1 | 8/2007 | Schaeffer |
| 2007/0179593 A1 | 8/2007 | Fierens et al. |
| 2007/0179601 A1 | 8/2007 | Fierens et al. |
| 2007/0198078 A1 | 8/2007 | Berra et al. |
| 2007/0203566 A1 | 8/2007 | Arbefeuille et al. |
| 2007/0207186 A1 | 9/2007 | Scanlon et al. |
| 2007/0213800 A1 | 9/2007 | Fierens et al. |
| 2007/0219620 A1 | 9/2007 | Eells et al. |
| 2007/0244545 A1 | 10/2007 | Birdsall et al. |
| 2008/0021538 A1 | 1/2008 | Wright et al. |
| 2008/0027528 A1 | 1/2008 | Jagger et al. |
| 2008/0046065 A1 | 2/2008 | Hartley et al. |
| 2008/0065011 A1 | 3/2008 | Marchand et al. |
| 2008/0071343 A1 | 3/2008 | Mayberry et al. |
| 2008/0077226 A1 | 3/2008 | Ouellette et al. |
| 2008/0077227 A1 | 3/2008 | Ouellette et al. |
| 2008/0082158 A1 | 4/2008 | Tseng et al. |
| 2008/0114441 A1 | 5/2008 | Rust et al. |
| 2008/0132996 A1 | 6/2008 | Drasler et al. |
| 2008/0172122 A1 | 7/2008 | Mayberry et al. |
| 2008/0195191 A1 | 8/2008 | Luo et al. |
| 2008/0208175 A1 | 8/2008 | Beckman et al. |
| 2008/0262590 A1 | 10/2008 | Murray |
| 2008/0264102 A1 | 10/2008 | Berra |
| 2008/0269865 A1 | 10/2008 | Snow et al. |
| 2009/0163951 A1 | 6/2009 | Simmons et al. |
| 2009/0254165 A1 | 10/2009 | Tabor et al. |
| 2010/0030255 A1 | 2/2010 | Berra et al. |
| 2010/0030318 A1 | 2/2010 | Berra |
| 2010/0234932 A1 | 9/2010 | Arbefeuille et al. |
| 2010/0274340 A1 | 10/2010 | Hartley et al. |
| 2011/0208288 A1 | 8/2011 | Arbefeuille et al. |
| 2011/0218607 A1 | 9/2011 | Arbefeuille et al. |
| 2011/0251664 A1 | 10/2011 | Acosta De Acevedo |
| 2011/0307049 A1 | 12/2011 | Kao |
| 2011/0313503 A1 | 12/2011 | Berra et al. |
| 2012/0123517 A1 | 5/2012 | Ouellette et al. |
| 2012/0143305 A1 | 6/2012 | Berra et al. |
| 2012/0296413 A1 | 11/2012 | Arbefeuille et al. |
| 2013/0274856 A1 | 10/2013 | Arbefeuille et al. |
| 2013/0325099 A1 | 12/2013 | Berra |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0148890 A9 | 5/2014 | Ouellette et al. |
| 2014/0243952 A1 | 8/2014 | Parodi et al. |
| 2014/0277340 A1 | 9/2014 | White et al. |
| 2014/0288627 A1 | 9/2014 | Ouellette et al. |
| 2014/0316510 A1 | 10/2014 | Berra |
| 2015/0202066 A1 | 7/2015 | Berra et al. |
| 2015/0202068 A1 | 7/2015 | Arbefeuille et al. |
| 2015/0272755 A1 | 10/2015 | Arbefeuille et al. |
| 2016/0045350 A1 | 2/2016 | Berra |
| 2016/0081787 A1 | 3/2016 | Parodi |

FOREIGN PATENT DOCUMENTS

| | | |
|---|---|---|
| DE | 10 2006 053748 B3 | 4/2008 |
| EP | 0 873 733 A1 | 10/1998 |
| EP | 0 960 607 A1 | 12/1999 |
| EP | 0 696 447 B1 | 1/2000 |
| EP | 0 990 426 A1 | 4/2000 |
| EP | 1 177 779 A2 | 2/2002 |
| EP | 1 302 178 A2 | 4/2003 |
| EP | 1 358 903 A2 | 11/2003 |
| EP | 1 369 098 A1 | 12/2003 |
| EP | 1522270 A2 | 4/2005 |
| EP | 1 772 120 A2 | 4/2007 |
| EP | 1 923 024 A2 | 5/2008 |
| EP | 1 929 979 A2 | 6/2008 |
| EP | 1 440 673 B1 | 9/2008 |
| EP | 1 982 677 A2 | 10/2008 |
| EP | 1 508 313 B1 | 12/2008 |
| FR | 2 714 816 | 7/1995 |
| FR | 2 722 678 | 1/1996 |
| FR | 2 779 939 A1 | 12/1999 |
| WO | WO 95/23008 | 8/1995 |
| WO | WO 96/09013 | 3/1996 |
| WO | WO 96/23455 | 8/1996 |
| WO | WO 96/31174 | 10/1996 |
| WO | WO 96/38101 | 12/1996 |
| WO | WO 97/10778 A1 | 3/1997 |
| WO | WO 97/33532 | 9/1997 |
| WO | WO 98/20811 | 5/1998 |
| WO | WO 98/23242 | 6/1998 |
| WO | WO 98/42276 | 10/1998 |
| WO | WO 98/53761 A1 | 12/1998 |
| WO | WO 99/25273 | 5/1999 |
| WO | WO 99/37242 | 7/1999 |
| WO | WO 99/65420 | 12/1999 |
| WO | WO 00/02615 | 1/2000 |
| WO | WO 00/30562 | 6/2000 |
| WO | WO 00/78248 A1 | 12/2000 |
| WO | WO 01/17602 A1 | 3/2001 |
| WO | WO 01/21102 A1 | 3/2001 |
| WO | WO 02/28316 A2 | 4/2002 |
| WO | WO 03/015662 A1 | 2/2003 |
| WO | WO 04/000169 A1 | 12/2003 |
| WO | WO 2004/002370 A1 | 1/2004 |
| WO | WO 2004/071352 A1 | 8/2004 |
| WO | WO 2005/023149 A2 | 3/2005 |
| WO | WO 2005/034808 A1 | 4/2005 |
| WO | WO 2005/067819 A1 | 7/2005 |
| WO | WO 2005/081936 A2 | 9/2005 |
| WO | WO 2005/112821 A2 | 12/2005 |
| WO | WO 2006/019551 A1 | 2/2006 |
| WO | WO 2006/088638 A1 | 8/2006 |
| WO | WO 2007/008533 A1 | 1/2007 |
| WO | WO 2007/028086 A2 | 3/2007 |
| WO | WO 2007/092276 A2 | 8/2007 |
| WO | WO 2007/123956 A2 | 11/2007 |
| WO | WO 2008/031103 A2 | 3/2008 |
| WO | WO 2008/098252 A2 | 8/2008 |
| WO | WO 2009/023221 A1 | 2/2009 |
| WO | WO 2009/124124 A1 | 10/2009 |
| WO | WO 2010/005524 A2 | 1/2010 |
| WO | WO 2010/027485 A1 | 3/2010 |

(56) References Cited

FOREIGN PATENT DOCUMENTS

WO     WO 2010/105195 A2    9/2010
WO     WO 2013/154749 A1    10/2013

OTHER PUBLICATIONS

Notification Concerning Transmittal of International Preliminary Report on Patentability, International Application No. PCT/US2013/031702, Titled: "Vascular Prosthetic Delivery Device and Method of Use", Dated: Oct. 23, 2014.
Office Action, U.S. Appl. No. 13/829,508, Dated: Oct. 20, 2014.
Notice of Allowance, U.S. Appl. No. 13/829,508, Dated: Dec. 15, 2014.

* cited by examiner

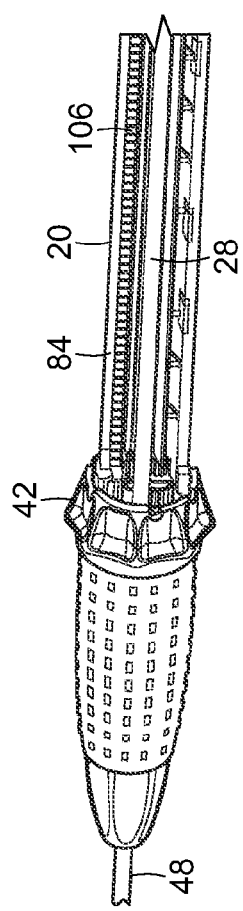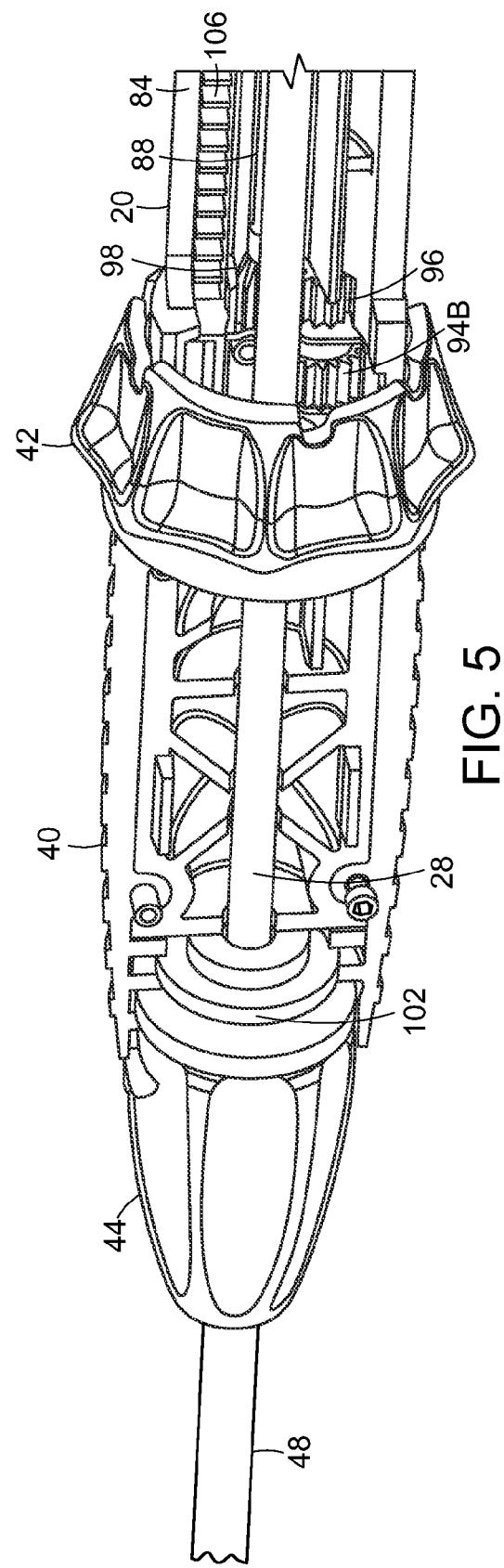

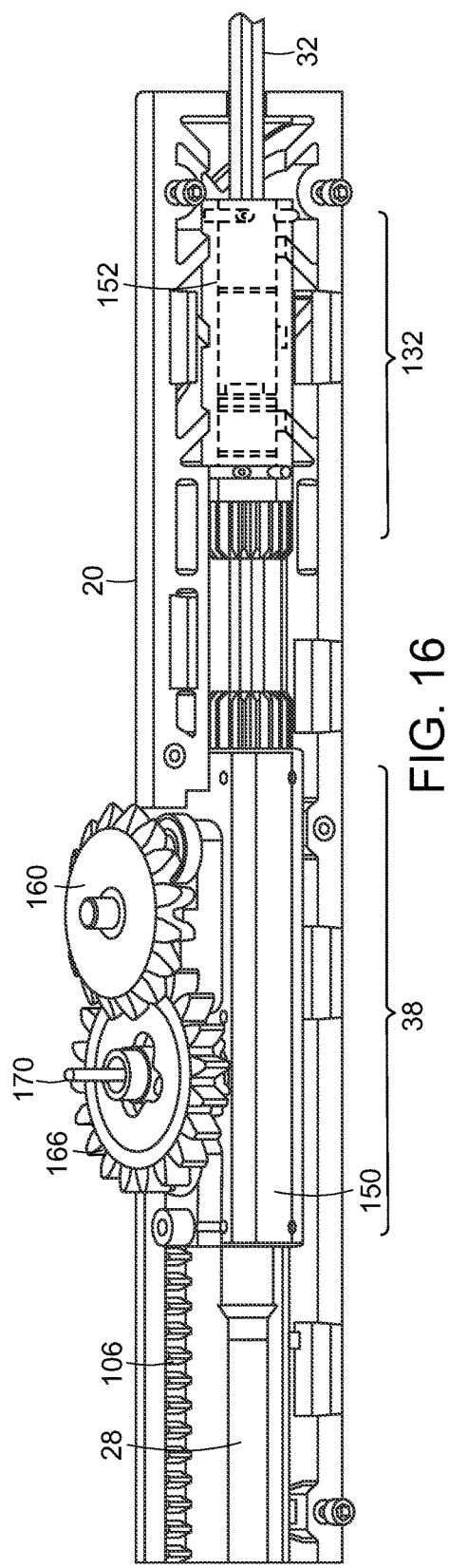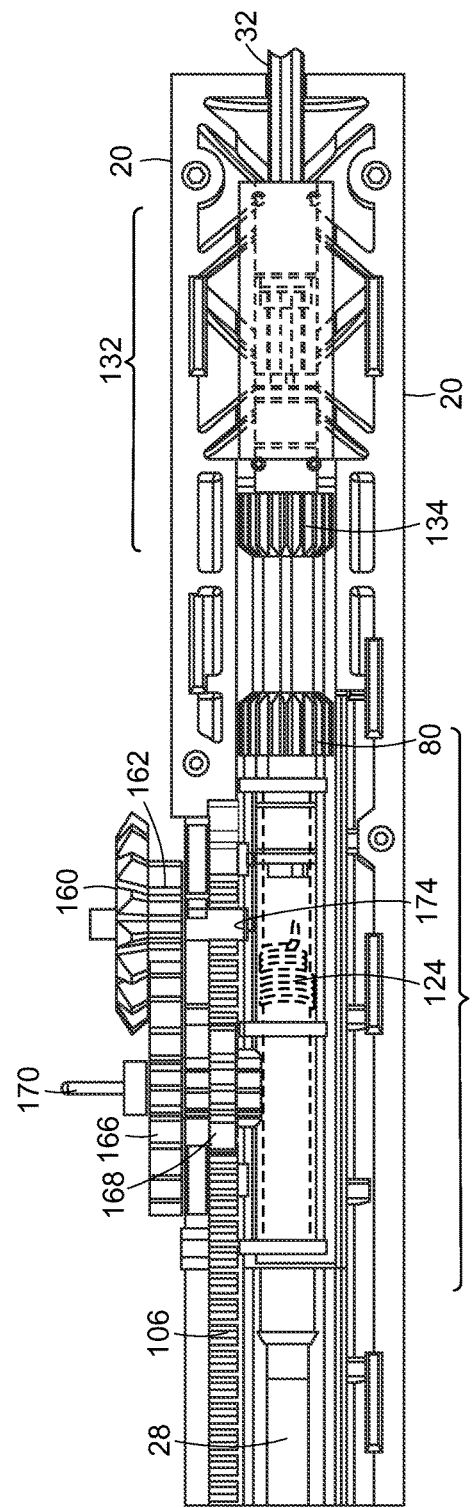

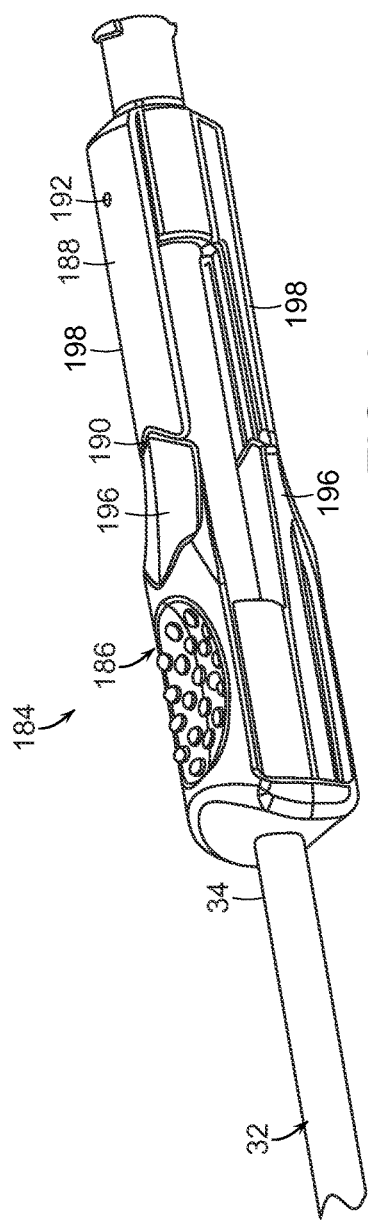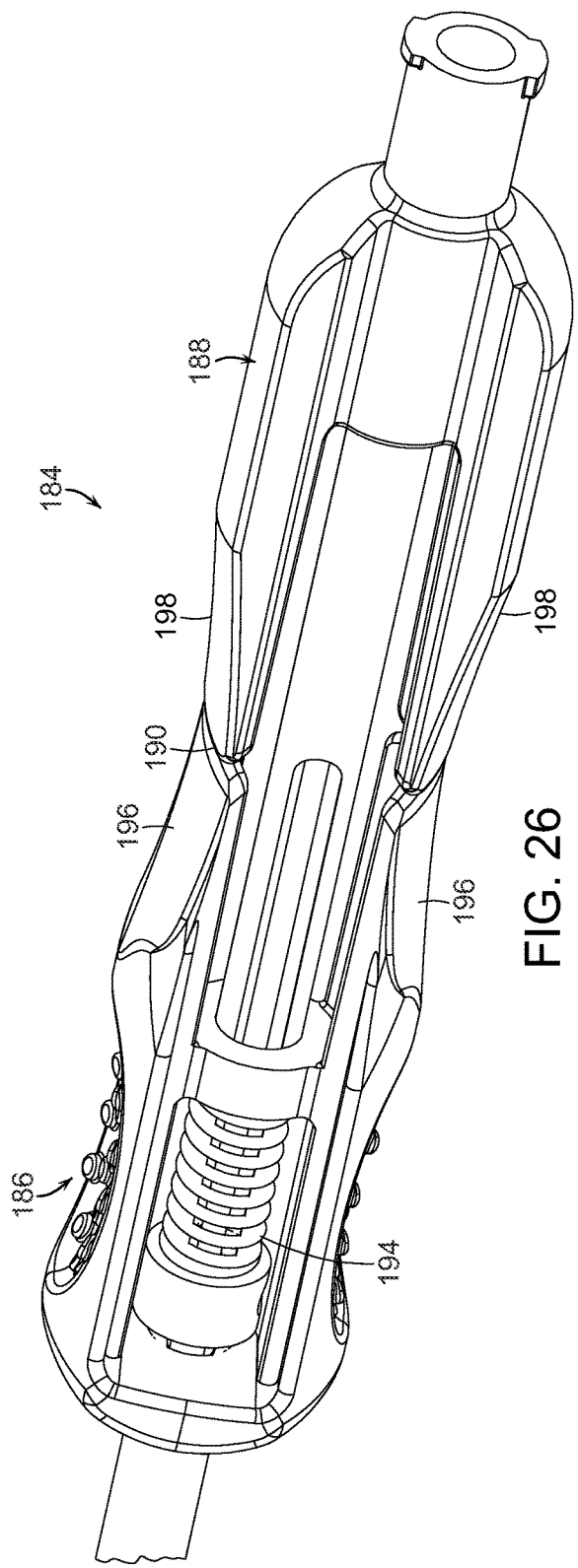

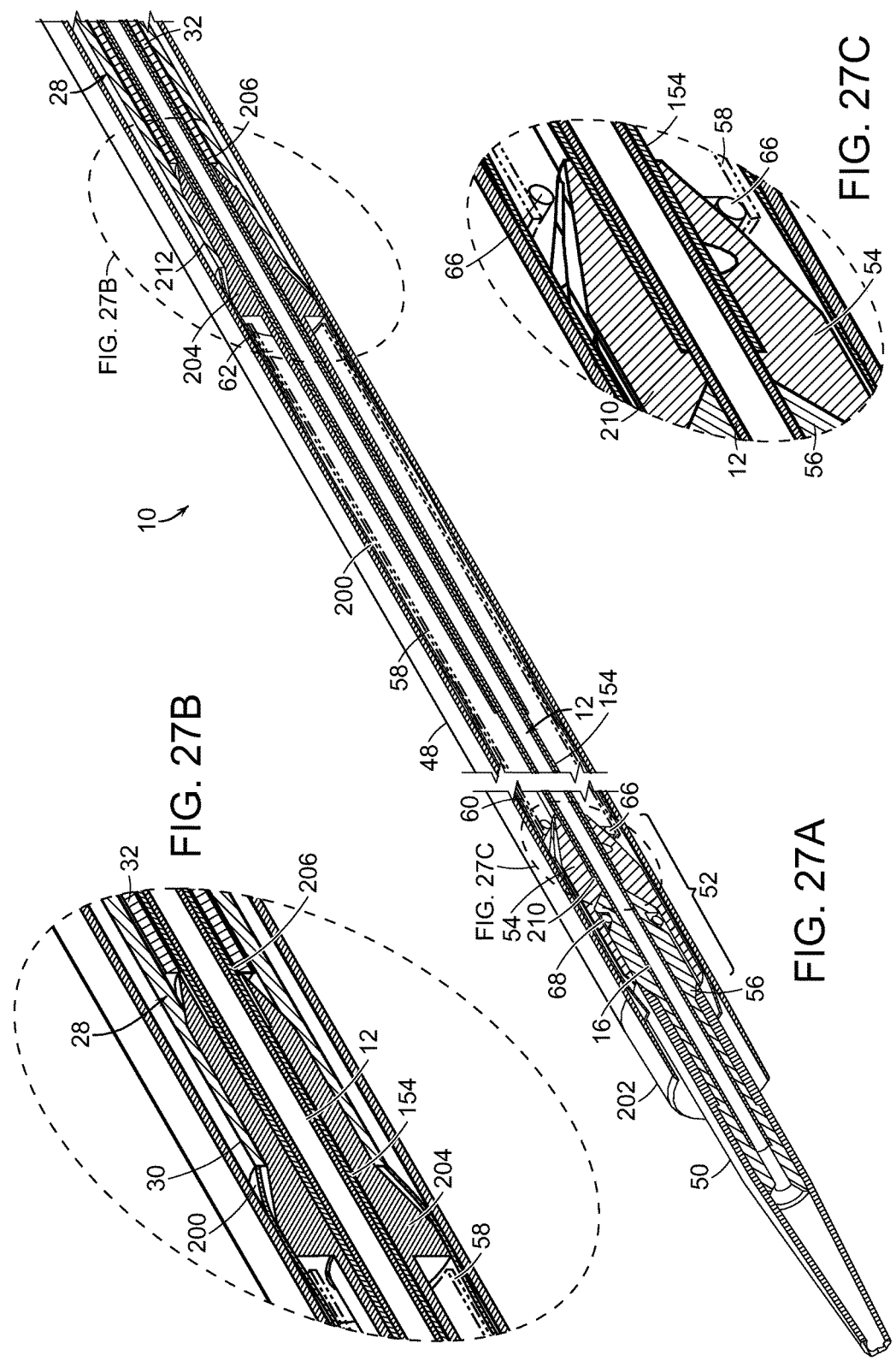

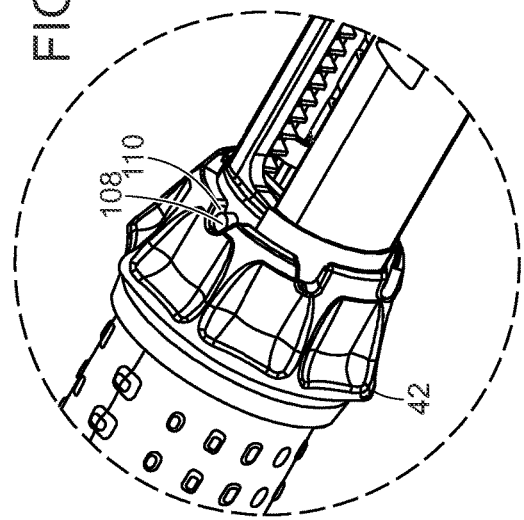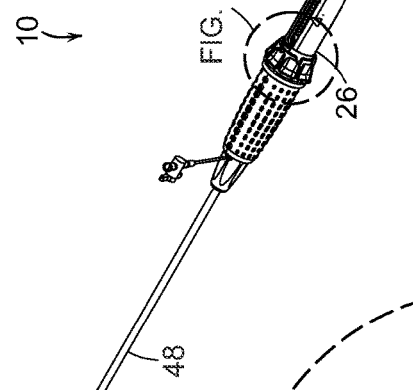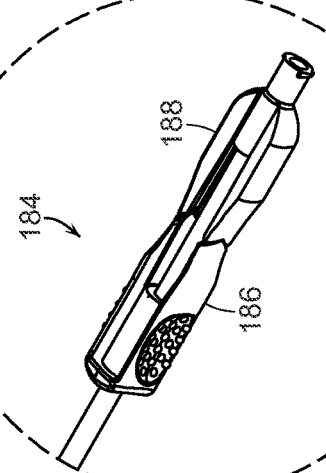

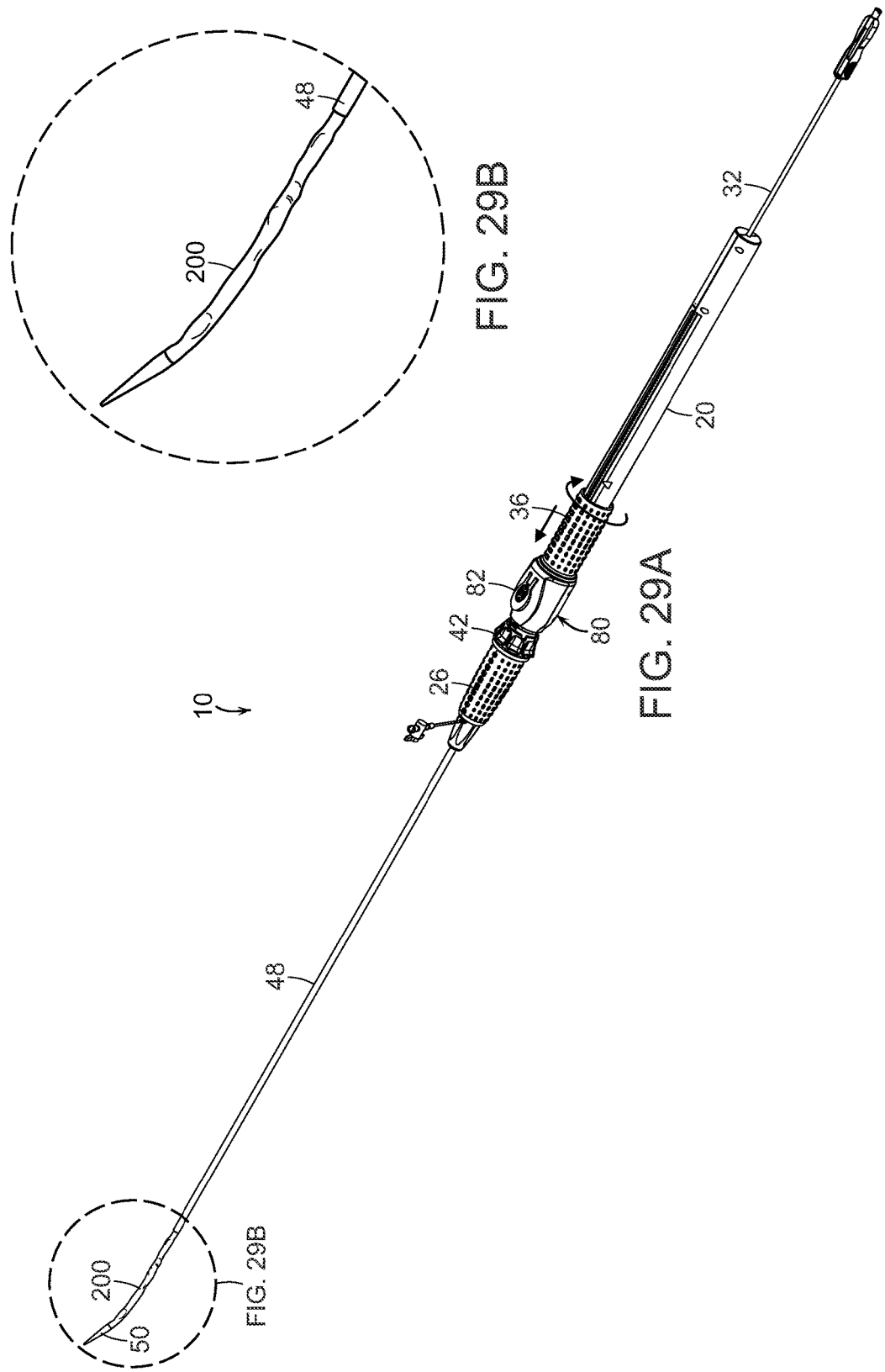

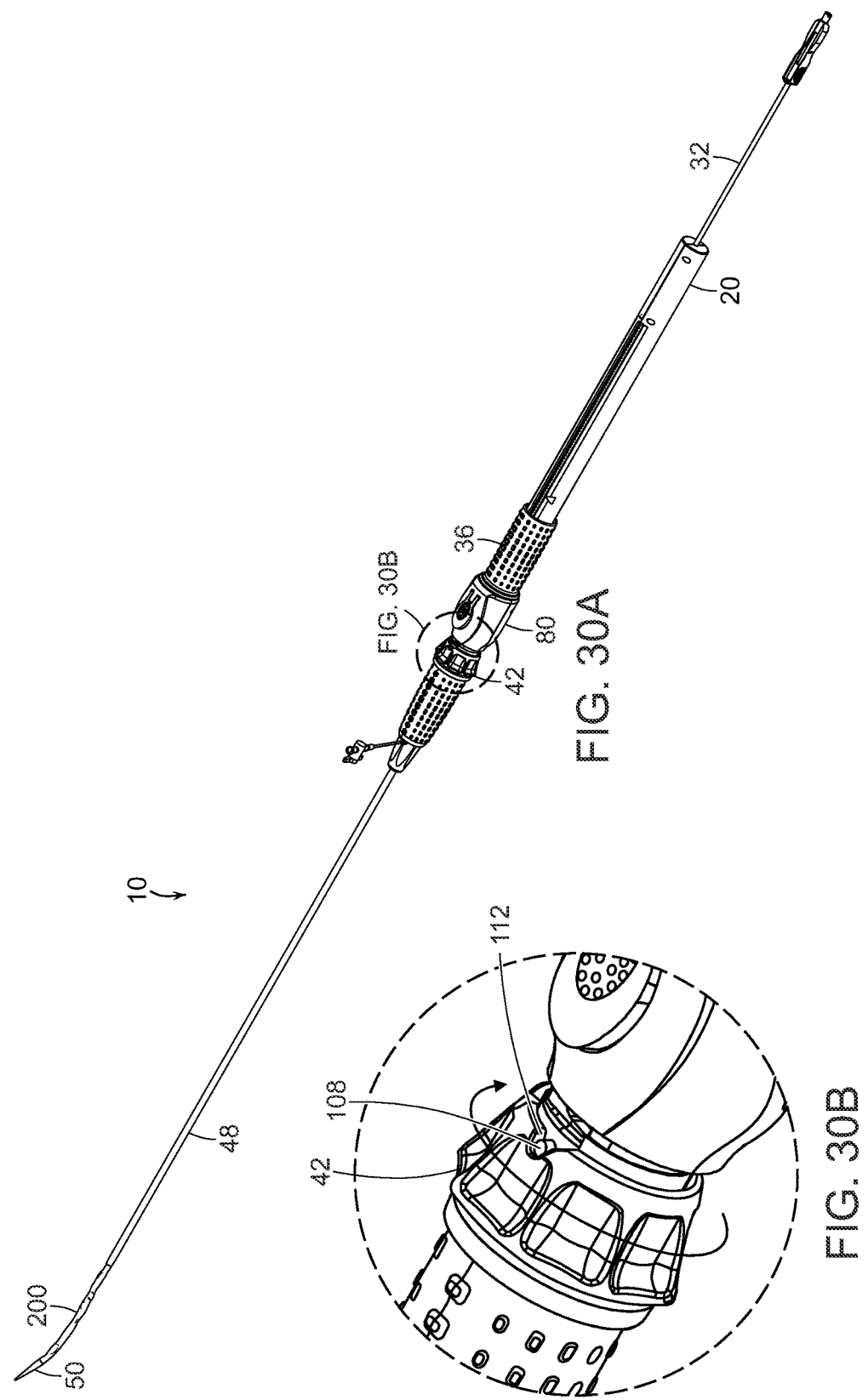

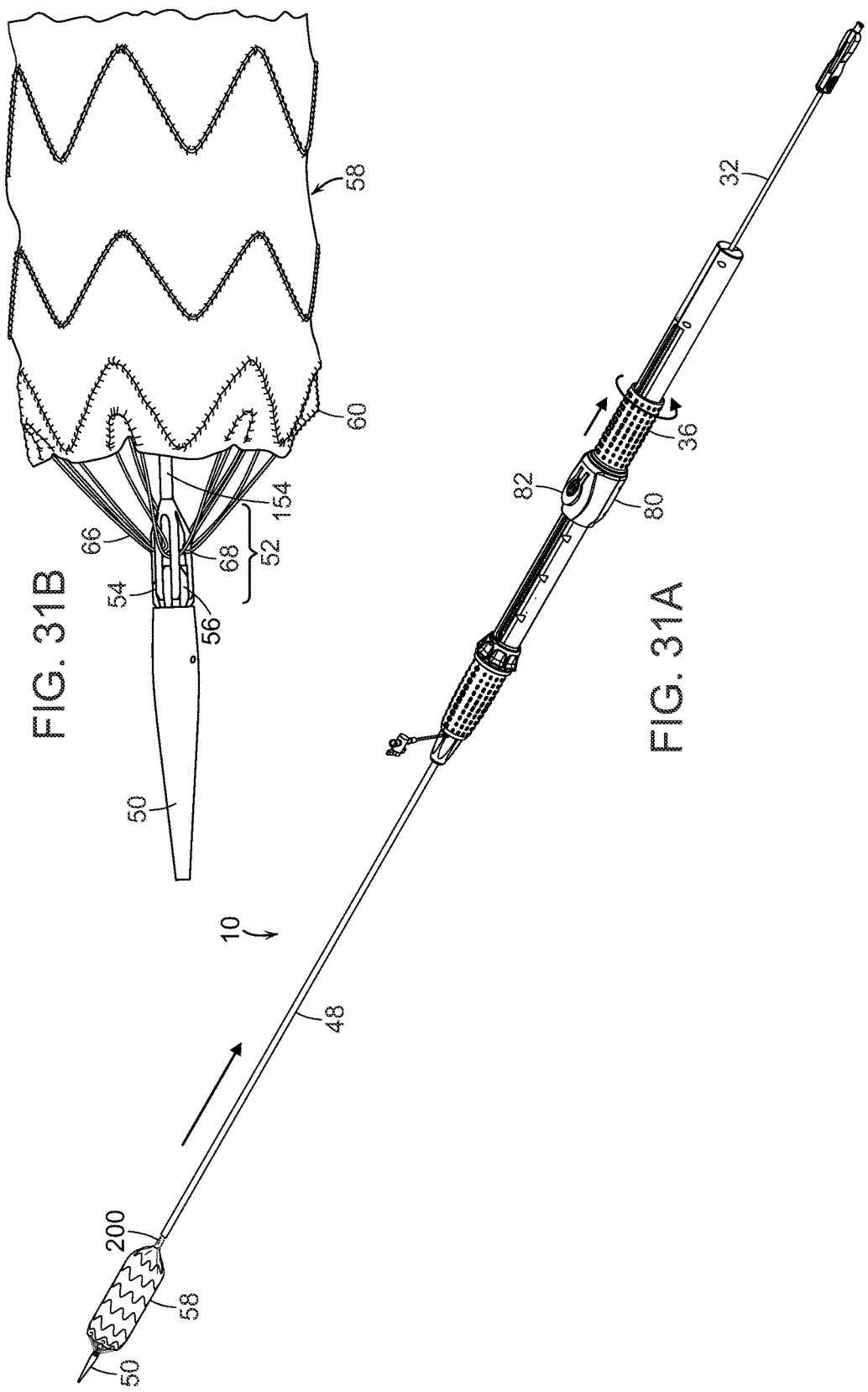

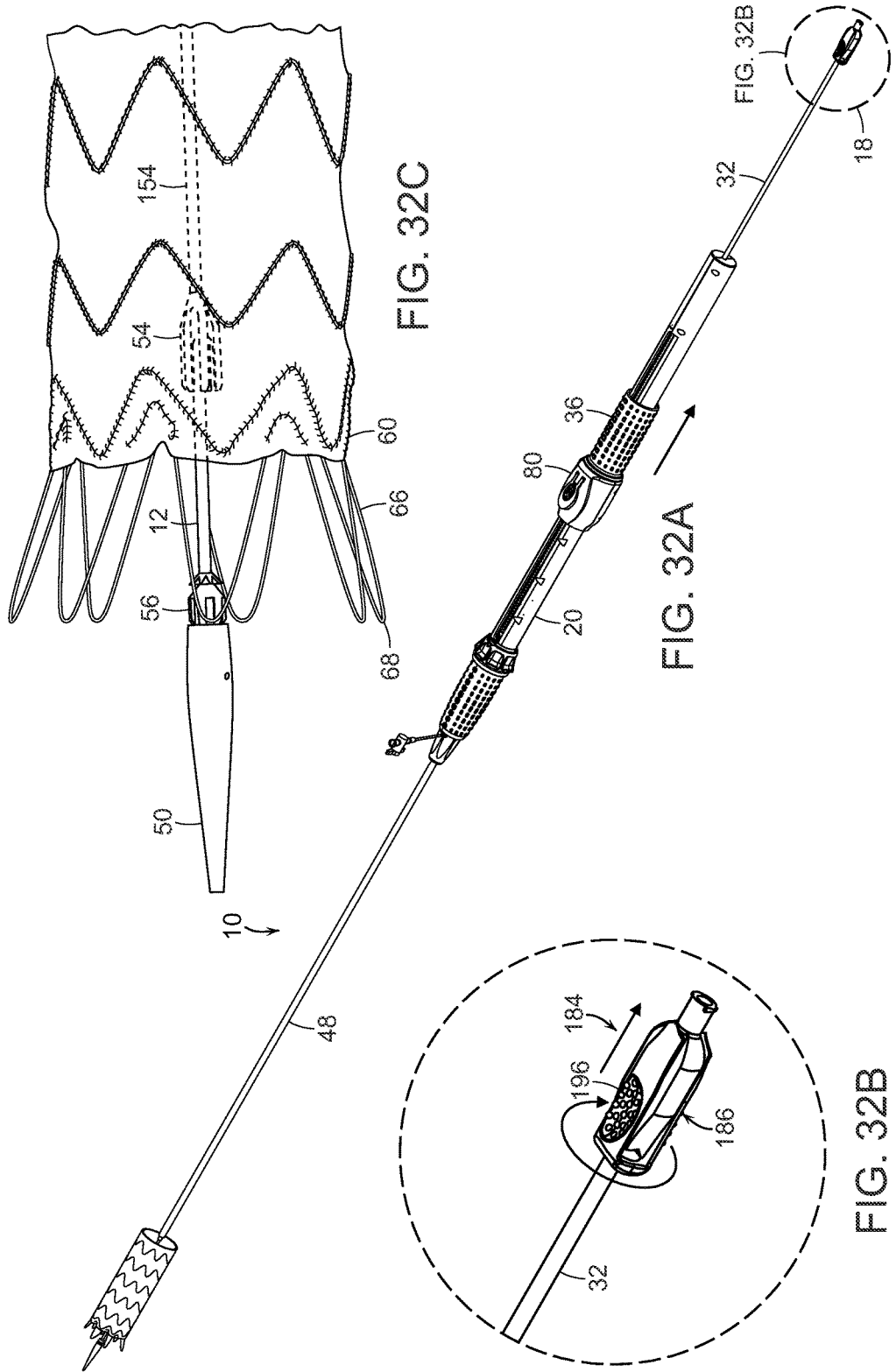

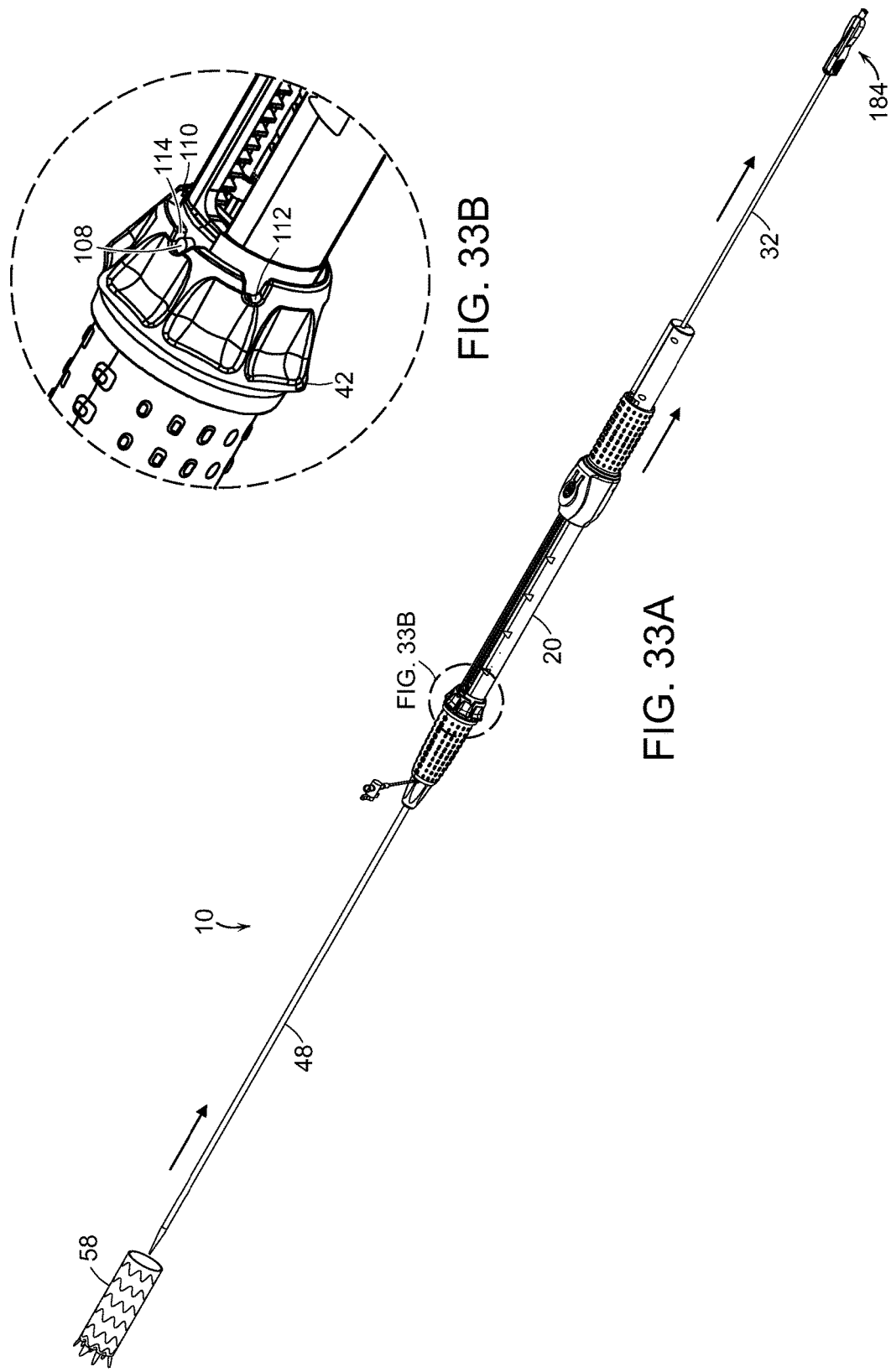

VASCULAR PROSTHETIC DELIVERY DEVICE AND METHOD OF USE

RELATED APPLICATION

This application is a divisional of U.S. application Ser. No. 13/829,508, filed Mar. 14, 2013, which claims the benefit of U.S. Provisional Application No. 61/623,235, filed on Apr. 12, 2012. The entire teaching of the above applications are incorporated herein by reference.

BACKGROUND OF THE INVENTION

An aortic aneurysm is an enlargement or bulge in a section of the aorta, which can be life-threatening. Treatment of aortic aneurysms remain a challenge. Endovascular repair has become a viable alternative to open repair of an aortic aneurysm. An endovascular approach results in insertion of an endovascular graft to exclude the aneurysm sac from blood flow. Once in place, the endovascular graft is expanded to create a new path for blood flow. The endovascular graft remains inside the aorta permanently through the use of a metal stent creating a tight fit and seal against the wall of the aorta. Currently, endovascular delivery devices have limitations on the precise control that the physician has in placement of the graft at the site of the aneurysm. Thus, there is a need to develop new and improved delivery devices and methods of using delivery devices to treat aortic aneurysms.

SUMMARY OF THE INVENTION

The invention is generally directed to a delivery device for implanting a vascular prosthesis, and to a method of use of the delivery device.

In one embodiment, the delivery device includes a guidewire catheter having a proximal end and a distal end, and a delivery assembly extending about the guidewire catheter. The delivery assembly includes a handle body, a delivery catheter, a push rod, a proximal handle and a locking mechanism. The handle body has a major longitudinal axis, a proximal end and a distal end. The delivery catheter has a distal end extending from within the distal end of the handle body and about the guidewire catheter. The push rod extends about the guidewire catheter and within the delivery catheter. The push rod is fixed to the guidewire catheter at a proximal end of the guidewire catheter proximal to the handle body. The proximal handle extends about the handle body and is axially fixed to the delivery catheter, wherein the proximal handle is selectively fixed to the push rod, and wherein the proximal handle is rotatable about the handle body and rotation of the proximal handle about the handle body translates to longitudinal movement of the delivery catheter and, selectively, of the push rod relative to the handle body. The locking mechanism at the handle body selectively engages the proximal handle with the push rod.

In an embodiment, the delivery device includes an actuator at the proximal handle that selectively disengages the proximal handle from the handle body, whereby rotation of the proximal handle is independent of longitudinal movement of the delivery catheter relative to the handle body. In another embodiment, the proximal handle includes an end that defines teeth that move transversely to a major longitudinal axis of the handle body when the proximal handle is rotated about the handle body. In this embodiment, the delivery device further includes a gear rack extending along the major longitudinal axis of the handle body, a linking gear engaging the teeth of the proximal handle end, the linking gear being rotatable about an axis transverse to the axis of rotation of the proximal handle, and a pinion gear. The pinion gear engages the gear rack and the linking gear, whereby rotation of the proximal handle about the handle body translates to the longitudinal movement of the delivery catheter and, selectively, of the push rod relative to the handle body. The actuator selectively disengages the linking gear from the pinion gear, thereby selectively disengaging rotation of the proximal handle from longitudinal movement of the proximal handle along the handle body.

In still another embodiment, the actuator of the delivery device includes an actuator housing, a push-button, a pinion gear extension, a ball bearing and a frustoconical center-pin. The actuator housing extends about the handle body and is rotatably linked to the proximal handle, whereby the actuator housing is movable along the handle body without rotating about the handle body while the proximal handle rotates about the handle body. The push-button is located at the actuator housing. The pinion gear extension defines a coaxial opening that is coaxial with the pinion gear and defines at least one lateral opening that extends laterally from the coaxial opening. The ball-bearing sits at least partially within the lateral opening and locks the relative rotation of the linking gear and the pinion gear when displaced to extend radially beyond the pinion gear extension. The frustoconical center-pin is biased radially outward from the major longitudinal axis of the handle body and abuts the push-button, whereby the frustoconical center-pin displaces the ball bearing radially outward through the lateral opening and locks the relative rotation of the linking gear and the pinion gear by the outward bias, thereby causing longitudinal movement of the proximal handle along the handle body when the proximal handle is rotated about the handle body and, when the push-button is depressed, selectively disengages the linking gear from pinion gear, thereby selectively disengaging rotation of the proximal handle from the longitudinal movement of the proximal handle along the handle body.

Another embodiment of the delivery device of the invention includes a distal grip at the distal end of the handle body, and the locking mechanism includes a shifting knob, a drive shaft, a drive gear and a first locking component. The shifting knob is located at the distal grip and is rotatable about the handle body and defines teeth along the inside of the shifting knob that move transversely to the major longitudinal axis of the handle body when the shifting knob is rotated about the handle body. The locking mechanism has at least two fixed positions relative to the handle body. The drive shaft has a proximal end and a distal end, wherein the distal end defines teeth that engage directly or indirectly, the teeth of the shifting knob, and extend along a major longitudinal axis of the driveshaft. The drive gear is along the drive shaft and defines teeth that engage, directly or indirectly, the teeth along the drive shaft, whereby the shifting knob is engaged with the drive gear at all positions of the shifting knob. The first locking component extends about the push rod and is linked to the proximal handle and the drive gear, whereby, in a first position of the shifting knob, the first locking component engages the proximal handle with the push rod, and rotation of the shifting knob from the first position to a second position causes rotation of the drive shaft which, in turn, causes rotation of the drive gear and disengagement of the first locking component from the push rod, thereby allowing independent movement of the delivery catheter along the longitudinal axis of the handle body relative to the push rod when the proximal handle is moved along major longitudinal axis of the handle body.

In another embodiment of the invention, the locking mechanism further includes a second locking component. The second locking component extends about the push rod, is fixed to the handle body, and is linked to the shifting knob through the drive shaft, whereby rotation of the shifting knob from the first position to the second position causes engagement between the handle body and the push rod, thereby preventing longitudinal movement of the push rod relative to the handle body when the proximal handle is moved along the major longitudinal axis.

In yet another embodiment, the delivery device of the invention includes an apex delivery device that includes an apex clasp assembly and proximal clasp assembly. The apex clasp assembly includes a distal capture component at a distal end of the guidewire catheter, a proximal capture component in mateable relation to the distal capture component, and an apex release catheter having a proximal end, wherein the apex release catheter extends about the guidewire catheter and is fixed to the proximal capture component. The proximal clasp assembly includes a fixed component at the proximal end of the guidewire catheter and an outer coupling at the proximal end at the apex release catheter in mateable relation with the fixed component of the proximal clasp assembly, whereby movement of the outer coupling relative to the fixed component from a first position to a second position will cause relative movement of the proximal capture component relative to the distal capture component of the apex clasp assembly.

In still another embodiment, the invention includes the delivery device that includes a gear rack, a handle extending about the gear rack and defining teeth at an end of the handle, the handle being rotatable about the gear rack, a pinion gear that is rotatable about an axis that intersects with the axis of rotation of the handle and engages the gear rack, a linking gear that selectively rotates with rotation of the pinion gear, an actuator that selectively engages the pinion gear with the linking gear, and a delivery catheter fixed to the handle, whereby rotation of the handle selectively moves a delivery catheter relative to the gear rack upon engagement of the pinion gear with the linking gear by the actuator.

In yet another embodiment, the invention is a method for delivering a vascular prosthesis to a treatment site of a subject. The method includes advancing the vascular prosthesis, while mounted at a proximal end of the prosthesis to an apex delivery device fixed to a distal end of a guidewire catheter, to a position distal to a vascular treatment site of the subject. A proximal handle is rotated in a first direction about a handle body, having a distal end, of a delivery device through which the guidewire catheter extends. The guidewire catheter is disposed within a push rod that also extends through the handle body, wherein the guidewire catheter is fixed to the push rod, whereby rotation of the proximal handle causes longitudinal movement of the guidewire catheter and the push rod along the handle body to thereby at least partially advance the prosthesis to the treatment site, the prosthesis being advanced from within an outer catheter extending from a distal end of the handle body and about the prosthesis. The position of a first locking component securing the proximal handle to the push rod is shifted from a first position to a second position, wherein the first locking component disengages the proximal handle from the push rod and a second locking component engages the push rod with the handle body. The proximal handle is then rotated in a second direction, whereby a delivery catheter, having a distal end and extending about the push rod, is withdrawn along the push rod, and a delivery sheath extending from the distal end of the delivery catheter is at least partially retracted from about the prosthesis. The proximal end of the prosthesis is then released from the apex delivery device. The second locking component is shifted to disengage the push rod from the handle body, and the push rod and the guidewire catheter are withdrawn from within the prosthesis, thereby delivering the vascular prosthesis to the treatment site.

The delivery device and method of its use of the invention have many advantages. For example, rotation of the proximal handle to thereby advance the push rod and a vascular prosthesis at the end of the push rod provides increased control over movement of the vascular prosthesis during implantation at a treatment site. Further, selective engagement of the proximal handle and the push rod enables disengagement of the proximal handle from the push rod to thereby provide for controlled refraction of a delivery sheath from the vascular prosthesis by rotation of the proximal handle in an opposite direction to that which is employed to advance the vascular prosthesis to the treatment site. In addition, an actuator of the delivery device enables selective disengagement of the proximal handle from the handle body, whereby the proximal handle can be moved along the handle body without rotation of the proximal handle, thereby providing another degree of freedom of movement of the vascular prosthesis during advancement of the vascular prosthesis to the treatment site and during retraction of the delivery sheath from the prosthesis once the prosthesis has been advanced to the treatment site. The delivery device of the invention also has the advantage of causing engagement of the push rod with the handle body upon disengagement of the proximal handle from the push rod, thereby enabling withdrawal of the delivery sheath from the vascular prosthesis without entrainment of the vascular prosthesis while the delivery sheath is being retracted from the vascular prosthesis by movement of the proximal handle. Further, the apex delivery device is controllable at a proximal end of the push rod and guidewire catheter, thereby enabling selective release of a proximal end of the vascular prosthesis at the treatment site while remaining components of the delivery device remain stationary. In addition, the push rod can be disengaged from both the handle body and the proximal handle, thereby enabling retraction of the push rod, guidewire catheter and apex delivery device from within the vascular prosthesis once it has been implanted at the delivery device, thereby minimizing potential disruption of the vascular prosthesis once it has been implanted.

BRIEF DESCRIPTION OF THE DRAWINGS

FIG. 4 is a perspective view of a shifting knob, distal handle, distal handle nose, and a cross-sectional view, in part, of a handle body and delivery catheter of another embodiment of the invention.

FIG. 5 is a partial cutaway section of the portion of the embodiment of the delivery device of the invention shown in FIG. 4.

FIG. 16 is a perspective view of the first locking component housing and the second locking component housing within a cutaway view of the handle body, along with a perspective view of the linking gear assembly and the pinion gear assembly of the actuator.

FIG. 17 is a side view of the representation of the invention, as shown in FIG. 16.

FIG. 25 is a perspective view of one embodiment of a proximal clasp assembly of one embodiment of the invention.

FIG. 26 is a partial cutaway of the proximal clasp assembly shown in FIG. 25.

FIGS. 27A-27C are perspective sectional views of the distal end of the delivery device shown in FIG. 1.

FIG. 28A is a perspective view of the shifting knob in the first position, wherein the push rod is fixed to the proximal handle and the prosthesis is undeployed.

FIG. 28B is a detailed perspective view of proximal clasp assembly in a first position, whereby the apex clasp assembly is unopened.

FIG. 28C is a detailed perspective view of the shifting knob in the first position.

FIG. 29A is a perspective view of the delivery device of FIGS. 28A-28C showing advancement of the delivery sheath containing the prosthesis when the shifting knob is in a second position, wherein the push rod is fixed to the handle body.

FIG. 29B is a detailed perspective view of advancement of the delivery sheath of FIG. 29A.

FIG. 30A is a perspective view of the delivery device of FIGS. 29A, 29B showing advancement of the delivery sheath.

FIG. 30B is a detailed perspective view of the shifting knob of FIG. 30A in a second position.

FIG. 31A is a perspective view of the delivery device of FIGS. 30A, 30B, wherein the delivery sheath has been partially retracted from the prosthesis.

FIG. 31B is a representation of an apex clasp assembly of one embodiment of the invention in a closed position.

FIG. 32A is a perspective view of the delivery device of FIG. 31A, wherein the apex clasp assembly is opened by actuation of the proximal clasp assembly to thereby release the apices of the proximal stent of the prosthesis shown in FIG. 32C.

FIG. 32B is a representation of the proximal clasp assembly of FIGS. 25, 26, whereby an apex clasp assembly, not shown, has been opened.

FIG. 32C is a representation of the apex clasp assembly of one embodiment of the invention, in an open position.

FIG. 33A is a perspective view of the delivery device of FIG. 32A, wherein the shifting knob has been moved to the third position, whereby the push rod has been released from the proximal handle and the handle body and, wherein the push rod has been retracted from the fully deployed prosthesis.

FIG. 33B is a perspective view of the shifting knob in the third position as shown in FIG. 33A.

DETAILED DESCRIPTION OF THE INVENTION

While this invention has been particularly shown and described with references to example embodiments thereof, it will be understood by those skilled in the art that various changes in form and details may be made therein without departing from the scope of the invention encompassed by the appended claims.

Figure 1:
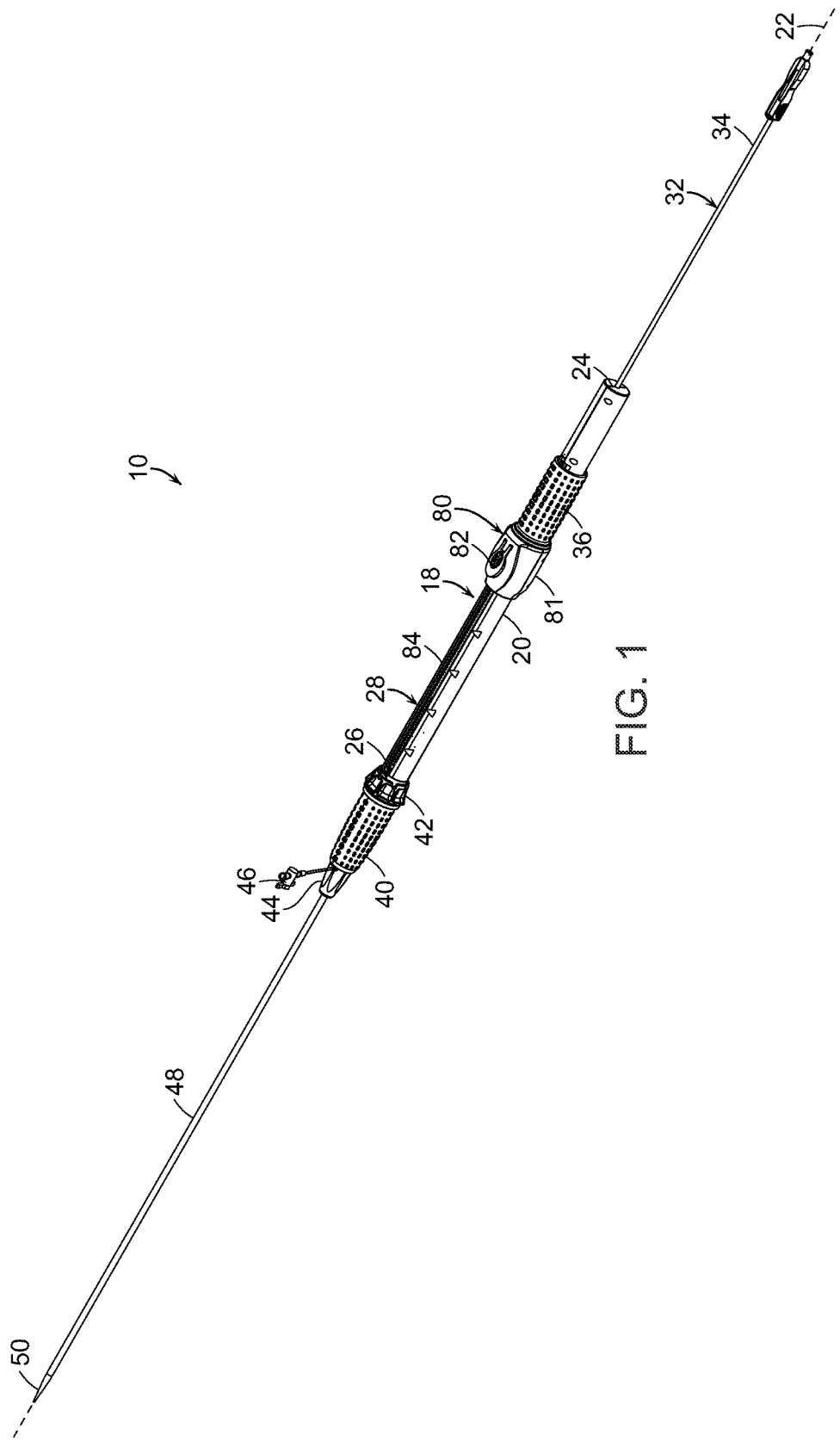
FIG. 1 is a perspective view of one embodiment of the delivery device of the invention.
Figure 9:
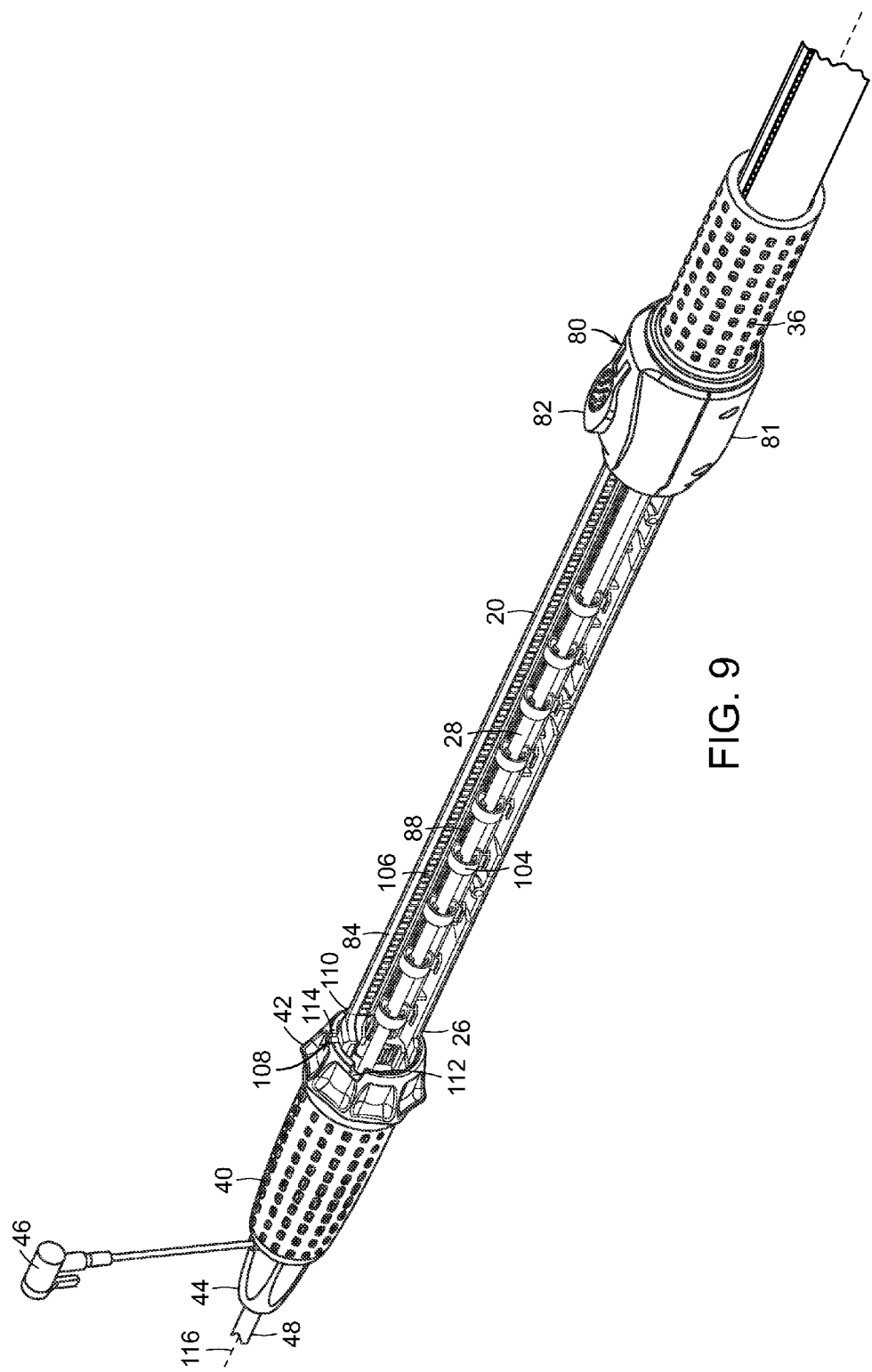
FIG. 9 is another embodiment of a partial cutaway of the delivery device of FIG. 1 showing an actuator and a push button at the proximal end of a slot defined by the handle body.
Figure 10:
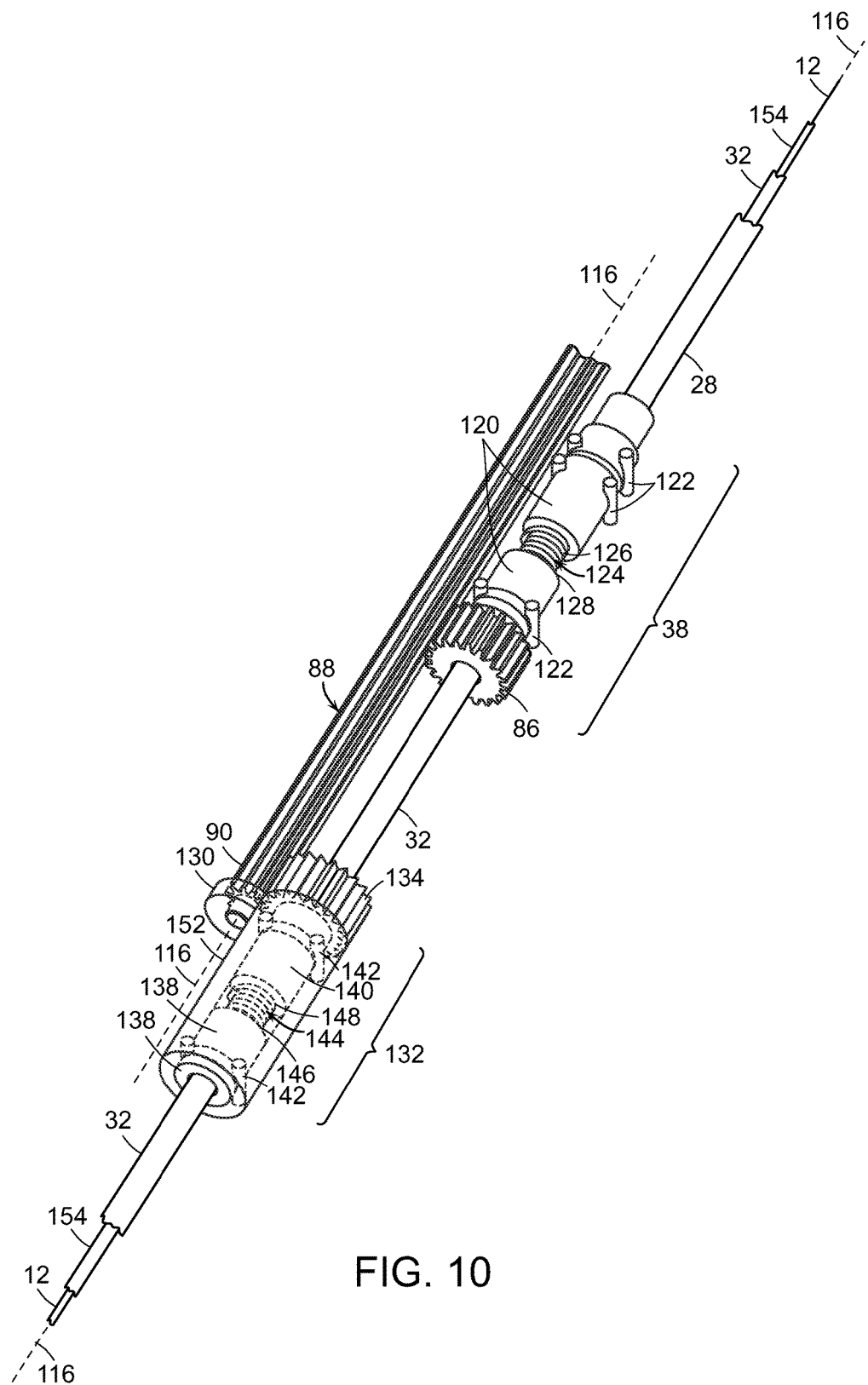
FIG. 10 is a perspective view of first locking component, and second locking component, and their relation to the drive shaft of the embodiment shown in FIG. 1.
Figure 11:
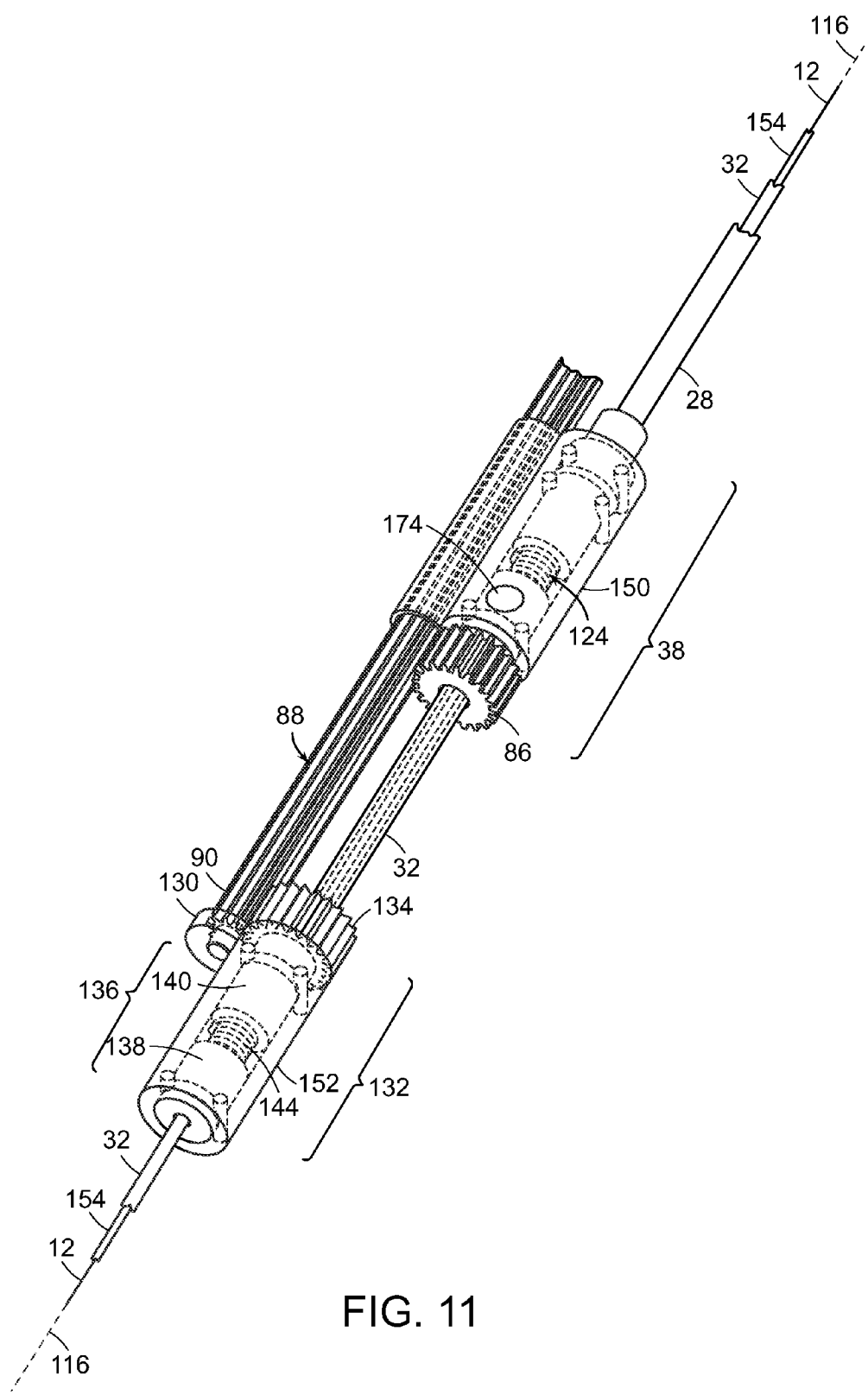
FIG. 11 is another representation of a first locking component and a second locking component, and a first locking component housing and a second locking component housing stabilizing the spatial relation between the first locking component and the second locking component, respectively, relative to the drive shaft of the embodiment of FIG. 1.

One embodiment, of the delivery device 10 of the invention is shown in FIG. 1. Delivery device 10 includes guidewire catheter 12 (FIGS. 10, 11) having a proximal end and a distal end. "Proximal," as a term employed herein with reference to the delivery device and its components, means relatively close to the surgeon operating the delivery device. "Distal," as a term employed herein with reference to the delivery device and its components, means relatively distal from the surgeon operating the delivery device. "Proximal," as a term employed herein with reference to the prosthesis, stent-graft and components, means relatively close to the heart of the patient. "Distal," as a term employed herein with reference to the prosthesis, stent-graft and components, means relatively distal from the heart of the patient. Returning to FIG. 1, delivery device 10 includes delivery assembly 18 that extends about the guidewire catheter (not shown). Delivery assembly 18 includes handle body 20 having major longitudinal axis 22, proximal end 24 and distal end 26. Delivery catheter 28 (FIG. 9) has distal end 30 (FIG. 27A) extending from within distal end 26 of handle body 20 and about the guidewire catheter (not shown). Push rod 32 extends about guidewire catheter 12 and within delivery catheter 28 (FIGS. 10, 11). Push rod 32 is fixed to guidewire catheter 12 at proximal end 34 of push rod 32 proximal to the handle body at pin 192 (FIG. 25). Referring back to FIG. 1, proximal handle 36 extends about handle body 20 and is axially fixed to delivery catheter 28. Proximal handle 36 is selectively fixed to push rod 32, wherein proximal handle 36 is rotatable about handle body 20 and rotation of proximal handle 36 about handle body 20 translates to longitudinal movement of delivery catheter 28 along longitudinal axis 22 and, selectively, of push rod 32 relative to handle body 20, as can be seen by comparing FIG. 12A with FIG. 12B. First locking mechanism 38 (FIG. 15) at handle body 20 selectively engages proximal handle 36 (FIGS. 12A and 12B) with push rod 32.

Figure 15:
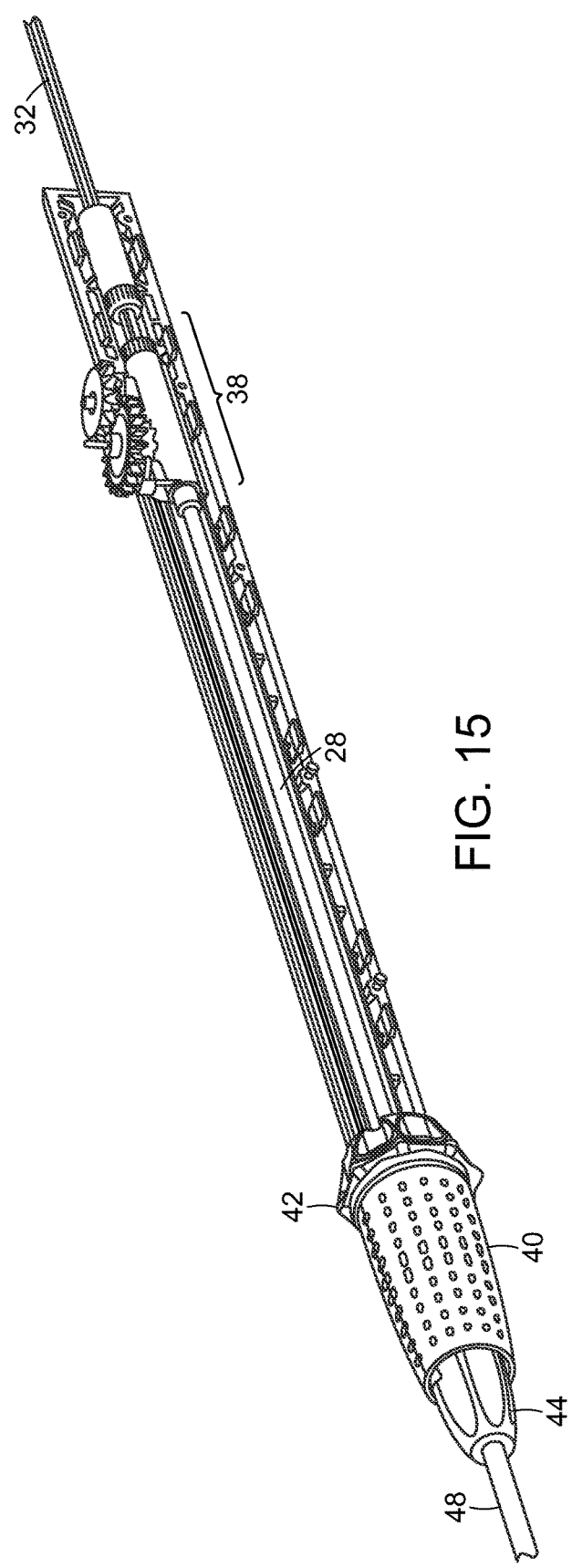
FIG. 15 is a partial cutaway of the embodiment of FIG. 1 showing the relation of the pinion and the linking gear assemblies relative to the first locking component housing and the relationship of the first locking component housing to the delivery catheter within the housing.

Distal handle 40 extends about handle body 20 at distal end 26 of handle body 20 and is distal to shifting knob 42 of first locking mechanism 38 ((FIG. 15). Distal handle nose 44 (FIG. 1) extends distally from distal handle 40 and includes flush port 46 for providing fluid communication between a solution source (not shown) and interior components of delivery device 10, as necessary, to hydrate contact between components of delivery device 10 and a vascular prosthesis (not shown) within a subject during implantation of the vascular prosthesis in the subject. Outer catheter 48 extends from distal handle nose 44 (FIG. 1).

Actuator 80 is linked to proximal handle 36, whereby proximal handle 36 can rotate about handle body 20 while push-button 82 at housing 81 of actuator 80 remains aligned with slot 84 defined by handle body 20. Depression of push-button 82 of actuator 80 selectively disengages proximal handle 36 from handle body 20, whereby rotation of proximal handle 20 is independent of longitudinal movement of delivery catheter 12 relative to handle body 20 along longitudinal axis 22.

Figure 2:
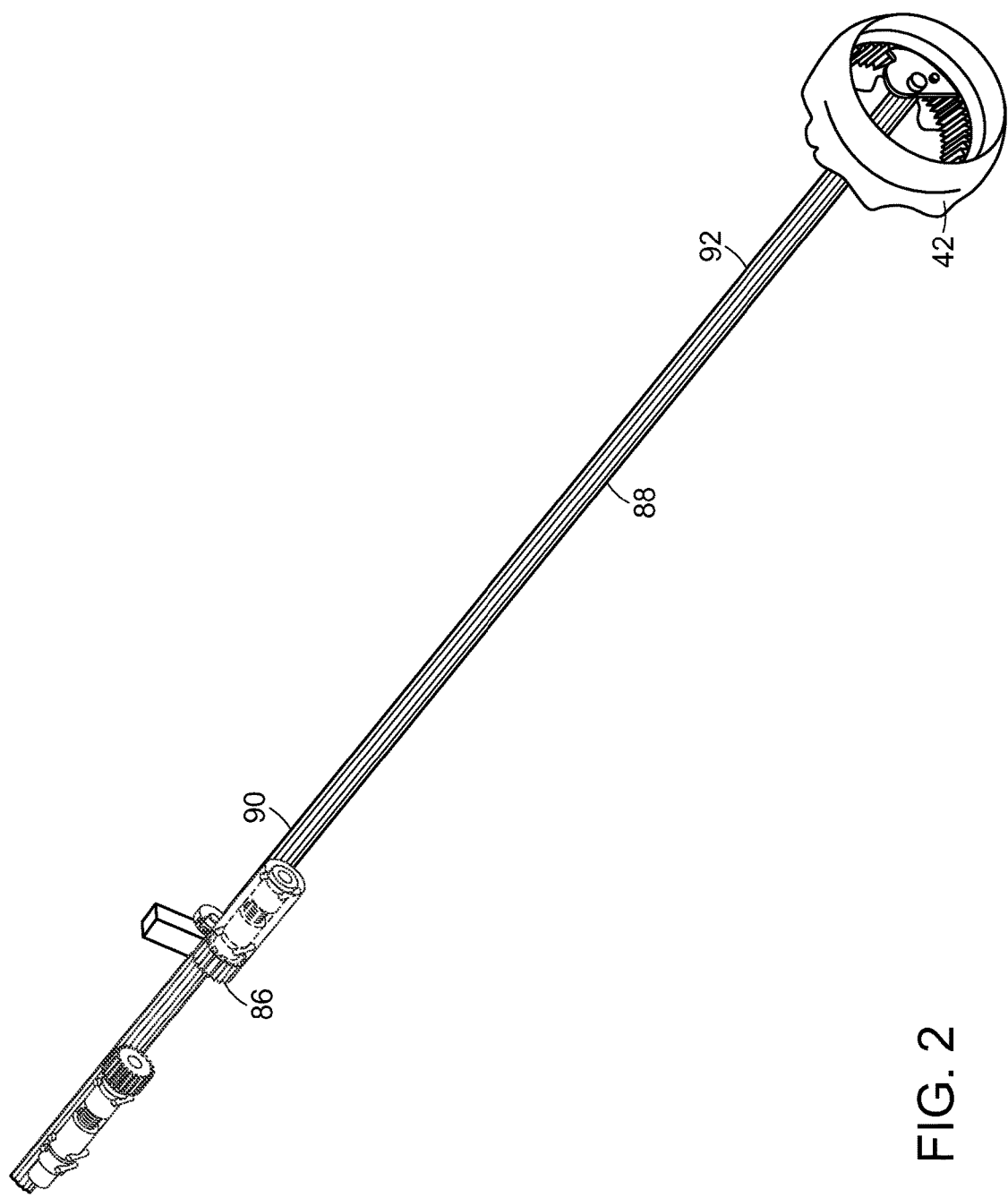
FIG. 2 is a perspective view of one embodiment of a shifting knob, driveshaft and actuator, of the invention.
Figure 3:
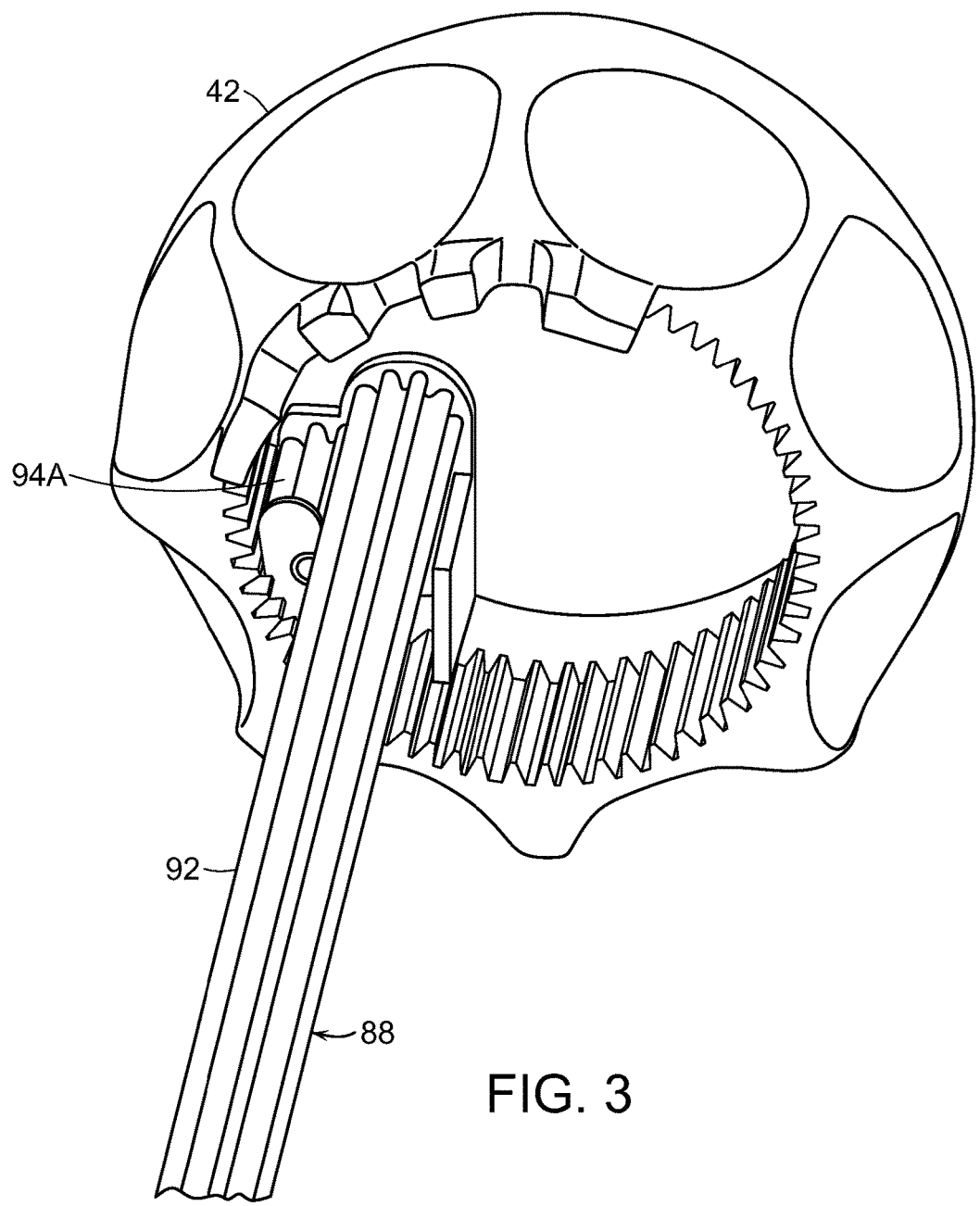
FIG. 3 is a perspective view of the shifting knob and driveshaft of the embodiment shown in FIG. 2.

As can be seen in FIG. 2, shifting knob 42 is linked to drive gear 86 by drive shaft 88. Drive shaft 88 has proximal end 90 and distal end 92, and runs along the interior of the handle body 20 (not shown). As can be seen in FIG. 3, shifting knob 42 is linked to drive shaft 88, in one embodiment, by intermediate gear 94A, whereby rotation of shifting knob 42 about handle body 20 causes rotation of drive shaft 88 by virtue of linkage between shifting knob 42 and drive shaft 88 by intermediate gear 94A. In this embodiment, shifting knob 42 is linked to drive shaft 88 indirectly, as opposed to direct linkage. "Direct linkage" would be direct contact with each other. Shifting knob 42 is rotatably linked to distal handle 40, which is fixed to distal end 26 of handle body 20, as shown in FIG. 1.

Figure 6:
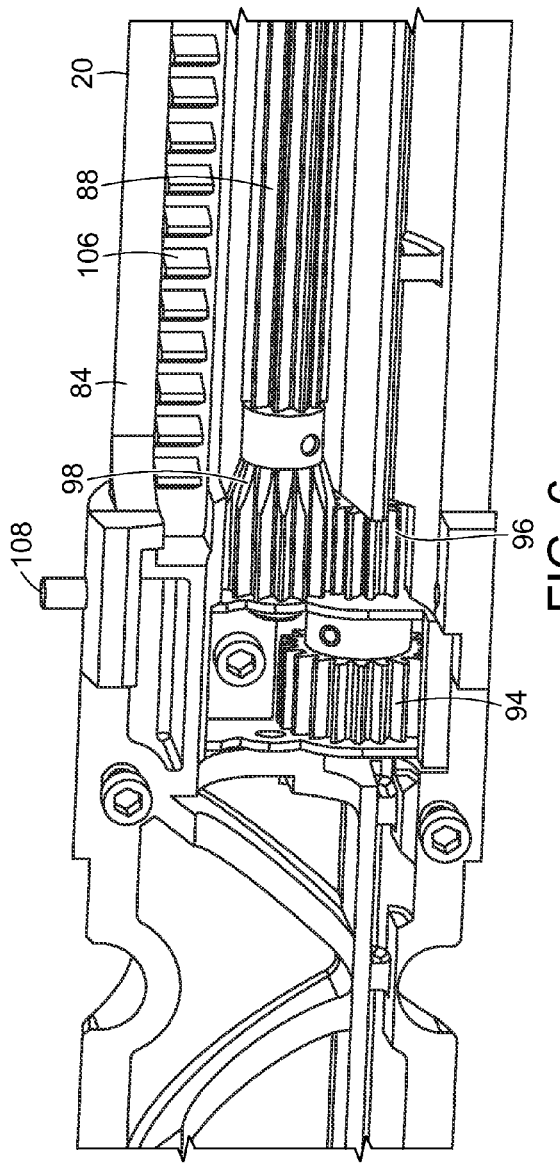
FIG. 6 is a partial cutaway section of a detail of a portion of the handle body, intermediate gear, reduction gear and connecting gear, all of which link the shifting knob with the driveshaft of the embodiment of the invention shown in FIG. 4.
Figure 7:
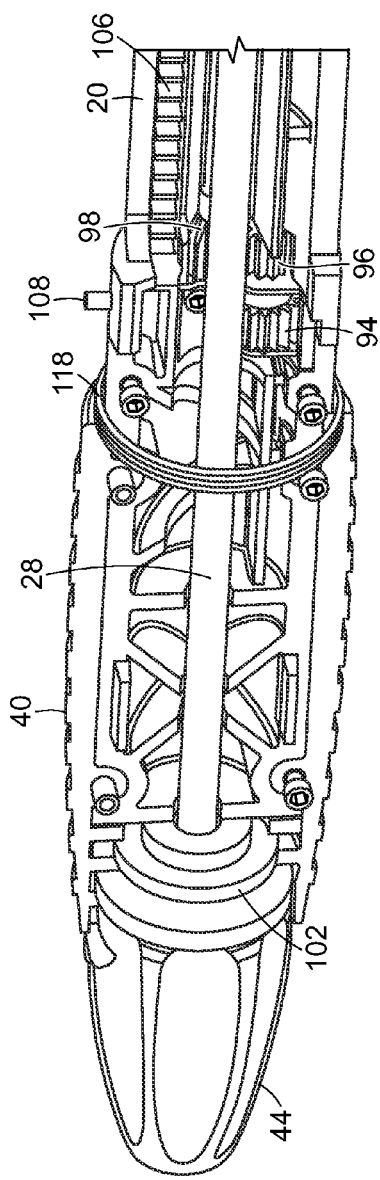
FIG. 7 is a partial cutaway view of the embodiment of FIG. 4, showing a cross-sectional view of the distal handle and a base to which outer catheter is connected at distal handle nose.

In another embodiment, shown in FIGS. 4 and 5, linkage between shifting knob 42 and drive shaft 88 includes a gear reduction at intermediate gear 94B that is linked to coaxial reduction gear 96 which, in turn, is linked to connecting gear 98 that is coaxially linked to drive shaft 88. By virtue of the gear reduction, the rate of rotation of shifting knob 42 relative to drive shaft 88 can be controlled by the relative dimensions of reduction gear 96 and connecting gear 98 (FIGS. 5, 6, 7). Typically, the rotation ratio, or reduction ratio, of shifting knob 42:drive shaft 88 is in a ratio of between about 1:2 and about 1:6. The relationship between reduction gear 96 and connecting gear 98 can be seen in greater detail in FIG. 6.

Figure 8:
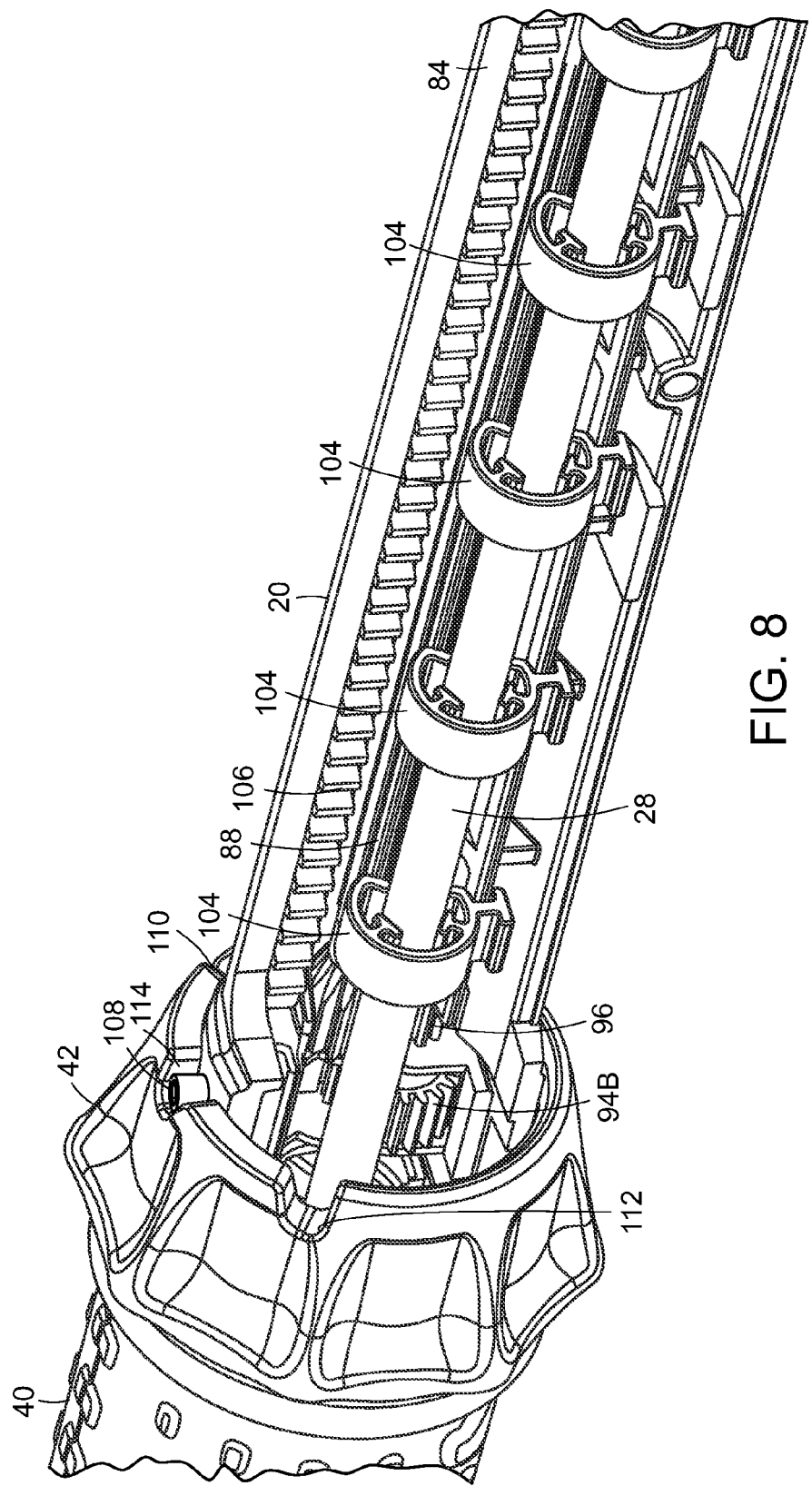
FIG. 8 is a partial cutaway, of the embodiment of FIG. 4 showing constricting rings extending about a delivery catheter.

As can be seen in greater detail in FIG. 7, delivery catheter 28 extends through handle body 20, distal handle 40 and distal handle nose 44. Referring back to FIG. 5, outer catheter 48 is linked to base 102, whereby outer catheter 48 is rotatable independently of handle body 20. As shown in FIG. 8, constricting rings 104 extend along the delivery catheter 28 within handle body 20. As shown in FIGS. 8 and 9, constricting rings 104 have an outside diameter greater than the width of slot 84, whereby constricting rings 104 will prevent application of longitudinal compressive force by proximal handle 36 on delivery catheter 28 from causing delivery catheter 28 to buckle and thereby move through slot 84 and outside of handle body 20. Constricting rings 104 also have an inside diameter slightly less than the outside diameter of delivery catheter 28, whereby constricting rings 104 will have an interference fit with delivery catheter 28, so that constricting rings 104 can move longitudinally along delivery catheter 28 if directed, but otherwise will remain in place relative to delivery catheter 28. Gear rack 106 extends longitudinally within handle body 20. Pin 108 at distal end of handle body 20 extends from distal end 26 of handle body 20 and is selectively slotted within slots 110,112,114 of shifting knob 42. Shifting knob 42 is longitudinally moveable along handle body 20 and is rotatable about handle body 20 sufficient to allow rotation of shifting knob 42 to move placement of pin 108 within any of slots 110,112,114 of shifting knob 42, which thereby causes rotation of intermediate gear 94. As a consequence, drive shaft 88 rotates about longitudinal axis 116 of drive shaft 88. Shifting knob 42 is a biased against pin 108 by spring 118 (FIG. 7).

As can be seen in FIG. 9, gear rack 106 and drive shaft 88 extend the length of slot 84. FIG. 10 shows the relation between drive shaft 88, push rod 32 and first locking mechanism 38. Push rod 32 extends through first locking mechanism 38 which, in turn, is engaged with drive shaft 88 at drive gear 86 of first locking mechanism 38. First locking mechanism 38 is fixed relative to proximal handle (not shown) at distal bearings 120 through which push rod 32 extends. Distal bearings 120 are linked to first locking component housing 150 by pins 122. First locking component 124 of first locking mechanism 38 is fixed relative to distal bearings 120 at distal end 126 and linked to drive gear 86 at proximal end 128, whereby rotation of drive shaft 88 and consequent rotation of drive gear 86 will further coil, or reduce coil, of first locking component 124, resulting in engagement or disengagement, respectively, of locking mechanism 38 and, consequently, proximal handle (not shown), with push rod 32. When first locking mechanism 38 is engaged with push rod 32, longitudinal movement of proximal handle (not shown) along drive shaft 88 and, thus, handle body 20, will cause longitudinal movement of push rod 32 along drive shaft 88 and handle body 20, as can be seen by comparing FIGS. 12A and 12B.

Referring back to FIGS. 10, 11, drive shaft 88 is rotatably fixed to handle body 20 (FIG. 9) at driveshaft bearing 130, which is part of second proximal locking component housing 152 at proximal end 90 of drive shaft 88. Second locking mechanism 132 includes translating gear 134 that is engaged with drive shaft 88 at proximal end 90 of the drive shaft 88 and is rotatably engaged with mechanism bearings 136 (FIG. 11), including proximal bearing 138 (FIG. 10) and distal bearing 140 (FIG. 10) which, in turn, are fixed relative to handle body 20 at pins 142. Proximal bearing 138 is radially and axially fixed to handle body 20. Distal bearing 140 is axially fixed to handle body 20. Second locking component 144 of second locking mechanism 132 is engaged with one of proximal bearing 138 at proximal end 146 of second locking component 144, and engaged with translating gear 134 at distal end 148 of second locking component 144, whereby rotation of drive shaft 88 and, consequently, rotation of translating gear 134 will tighten and engage, or loosen and disengage, second locking component 144 with push rod 32. When engaged with push rod 32, second locking component 144 causes push rod 32 to be fixed in location relative to handle body (not shown). When loosened and disengaged from push rod 32, push rod 32 is longitudinally movable relative to handle body (not shown). The orientation of first locking component 124 and second locking component 144 are reversed, whereby rotation of drive shaft 88 in one direction will, simultaneously, cause engagement and disengagement of first locking component 124 and second locking component 144 with push rod 32, respectively. Disengagement of first locking component 124 from push rod 32 is caused by movement of shifting knob 42 from a first position defined by pin 108 at slot 110 of shifting knob 42 to second position 112, defined by pin 108 at second slot 112 of shifting knob 42 (FIG. 9). The same movement from the first to second position of shifting knob 42 will simultaneously cause engagement of second locking component 144 with push rod 32, whereby push rod 32 will be fixed in position relative to handle body 20 at second locking component 144 regardless of movement of proximal handle 36 along longitudinal axis 116 of handle body 20. Referring back to FIGS. 8 and 9, positioning shifting knob 42, so that pin 108 is at intermediate slot 114 between the first slot 110 and second slot 112 of shifting knob 42, will cause both first locking component 124 and second locking component 144 to be disengaged from push rod 32.

As can be seen in FIG. 11, first locking component housing 150 fixes lateral movement of first locking component 124 and drive shaft 88, and second locking component housing 152 fixes the position of second locking component 144 and bearings 138,140 relative to proximal end 90 of drive shaft 88, respectively. Further, as can also be seen in FIG. 11, apex release catheter 154 extends within push rod 32 and guidewire catheter 12 extends within apex release catheter 154.

Figure 12:
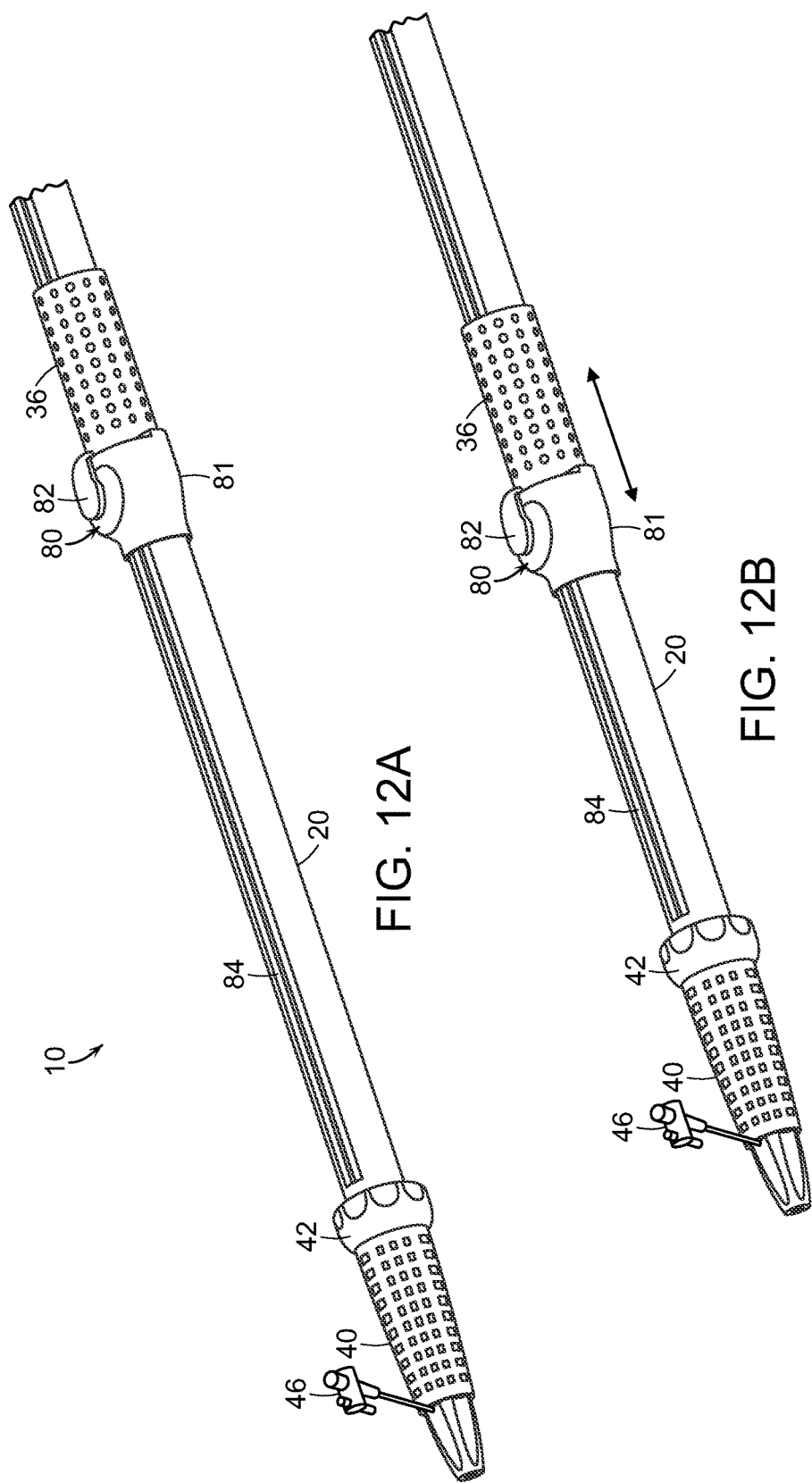
FIG. 12A is another perspective view of the embodiment of FIG. 1, showing displacement of the proximal handle and the actuator along the handle body consequent to rotating of the proximal handle about the handle body or depressing the push button of the actuator to thereby allow longitudinal movement of the actuator and the proximal handle without rotation of the proximal handle.
FIG. 12B is another perspective view of the embodiment of FIG. 1, wherein a proximal handle has been advanced along the handle body of the delivery system.

FIGS. 12A and 12B indicate relative movement of actuator 80 and proximal handle 36 along handle body 20. Rotation of proximal handle 36 about handle body 20, when push button 82 is in a first position, as shown in FIGS. 12A and 12B, will cause longitudinal movement of proximal handle 20 and actuator 80 along handle body 20. Upon depression of push button 82 to a second position essentially flush with actuator housing 81, rotation of proximal handle 36 will not cause longitudinal movement of proximal handle 36 or actuator along handle body 20. Rather, proximal handle 36 and actuator 80 will be movable along handle body 20 without rotation of proximal handle 36 about handle body 20.

Figure 13:
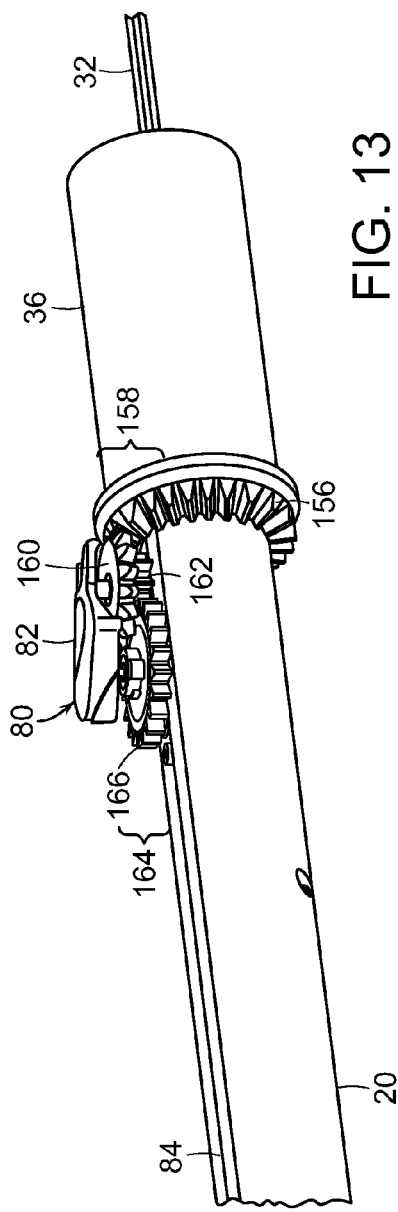
FIG. 13 is a detail of the proximal handle and the actuator at the handle body of the embodiment of the invention shown in FIG. 1, without the actuator housing.
Figure 14:
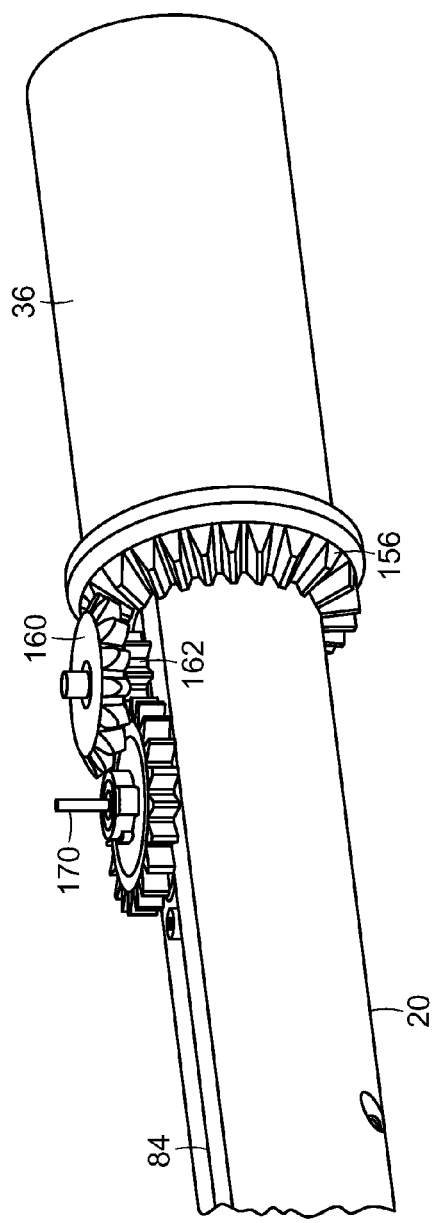
FIG. 14 is a perspective view of the detail of FIG. 13, without the push button of the actuator shown in FIG. 13.

As can be seen in FIGS. 13-15, teeth 156 of proximal handle 36 engage upper linking gear 160 of linking gear assembly 158. Linking gear assembly 158 is engaged with pinion gear assembly 164. Lower linking gear 162 of linking gear assembly 158 engages upper pinion gear 166 of pinion gear assembly 164. Pinion gear assembly 164 is linked to first locking component housing 150 (FIG. 11) through slot 84. Linking gear assembly 158 and pinion gear assembly 164 are components of actuator 80, referenced with respect to FIG. 1. FIG. 16 is a perspective view of actuator 80 of FIG. 1 (without housing 81 or pushbutton 82), of first locking component housing 150 and second locking component housing 152.

As can be seen in FIG. 17, upper pinion gear 166 is coaxial with lower pinion gear 168 which, in turn, engages gear rack 106. Referring back to FIGS. 16 and 17, delivery catheter 28 is linked to first locking component housing 150 and, thus, will move longitudinally along housing 150, with movement of proximal handle 36 and actuator 80 as shown in FIG. 1 regardless of whether first locking component 124 is engaged with push rod 32. Therefore, when upper pinion gear 166 engages lower pinion gear 168, rotation of proximal handle 36 (as shown in FIG. 1) about handle body 20 will cause rotation of linking gear assembly 158 (FIG. 13) and, consequently, rotation of pinion gear assembly 164 (FIG. 13) and movement of pinion gear assembly 164 (FIG. 13) along gear rack 106 (FIGS. 16 and 17), and movement of proximal handle 36 (FIG. 1) and actuator 80 (FIG. 17) along handle body 20. Further, while first locking component 124 is engaged with push rod 32, rotation of proximal handle 36 will cause longitudinal movement of push rod 32 along handle body 20. In all cases, movement of proximal handle 36 and actuator 80 along handle body 20 will always occur together, and will cause movement of delivery catheter 28 longitudinally along handle body 20.

However, as will be further explained below, depression of center pin 170 disengages upper pinion gear 166 from lower pinion gear 168. When upper pinion gear 166 is disengaged from lower pinion gear 168, rotation of proximal handle 36 about handle body 20 does not cause longitudinal movement of the proximal handle 36 and actuator 80 along handle body 20. Further, longitudinal movement of proximal handle 36 and actuator 80 along handle body 20 can be obtained simply by moving proximal handle 36 and actuator 80 along handle body 20 without rotation of proximal handle 36 about handle body 20 (FIGS. 1, 12A and 12B).

Figure 18:
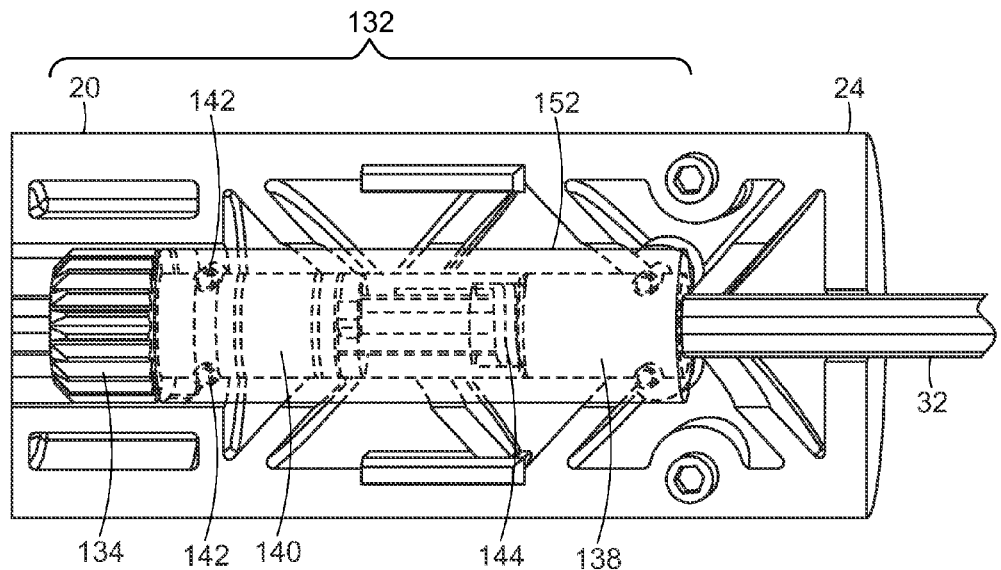
FIG. 18 is a partial cutaway of the distal end of handle body and second locking component shown in FIGS. 16 and 17.

FIG. 18 shows placement of the second locking component housing 152 within proximal end 24 of handle body 20 and second locking component 144 extending between bearings 138,140. As stated above, rotation of translating gear 134 by virtue of rotation of drive shaft 88 (FIGS. 10, 11) will cause engagement or disengagement of second locking component 144 with push rod 32 extending through second locking component 144 and, consequently, engagement and disengagement of push rod 32 with proximal end 24 of handle body 20.

Figure 19:
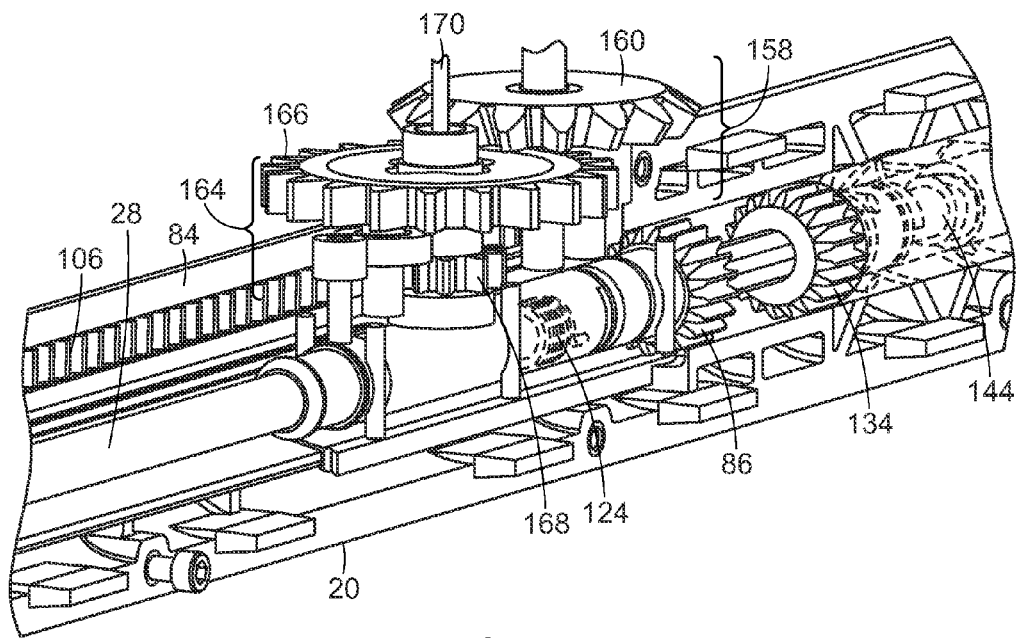
FIG. 19 is a perspective view of a partial cutaway of the actuator shown in FIG. 17.

FIG. 19 is another perspective view of linking gear assembly 158 and pinion gear assembly 164 of actuator 80 (FIG. 1).

Figure 20:
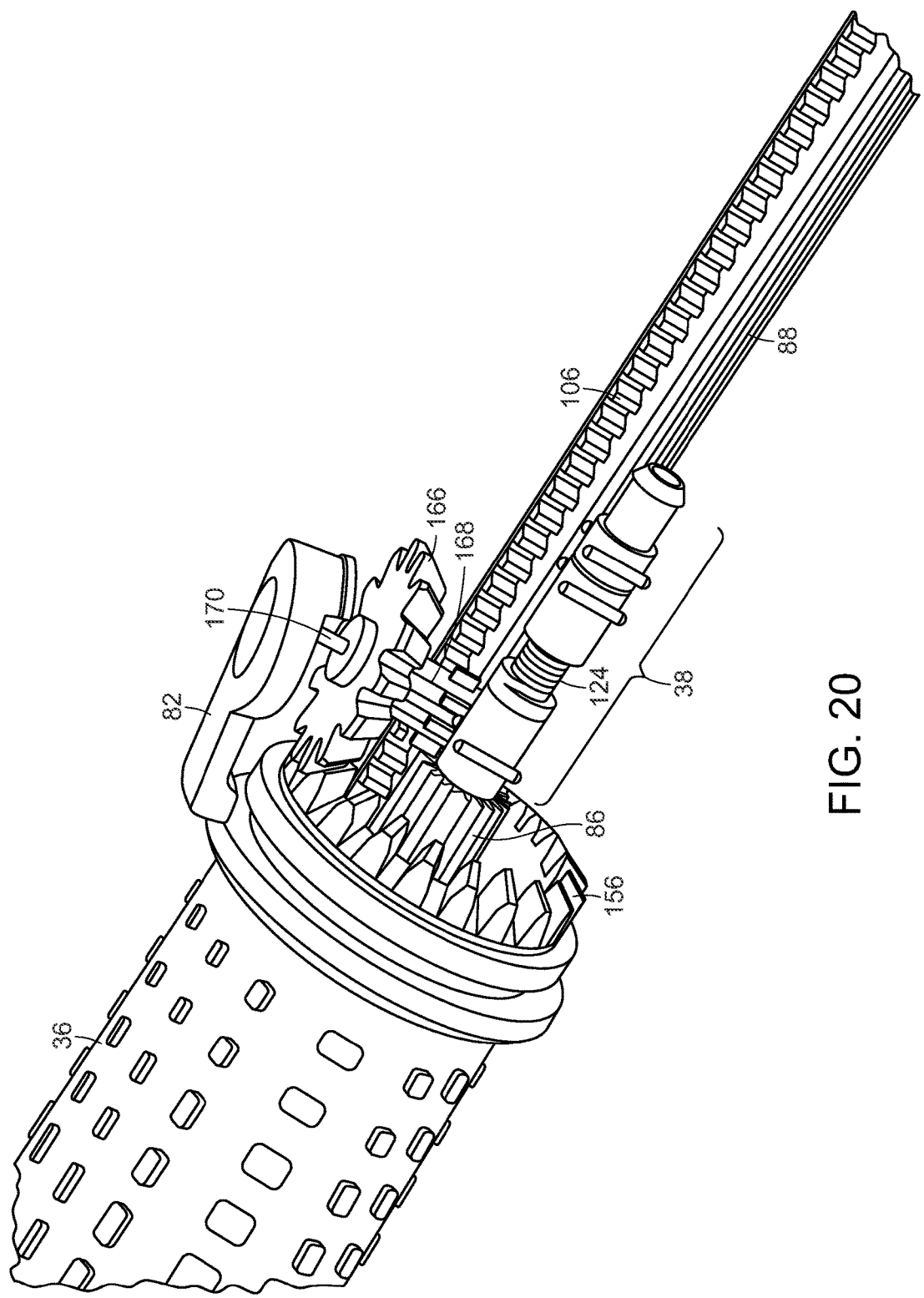
FIG. 20 is a perspective view of a rack and proximal handle of the embodiment shown in FIG. 1, and an alternate embodiment of the actuator of the invention, lacking a linking gear assembly.

As an alternative embodiment, shown in FIG. 20, push button 82 rests atop center-pin 170, which extends through upper pinion gear 166. As can also be seen in FIGS. 20 and 21, lower pinion gear 168 is engaged with gear rack 106 and includes pinion gear extension 169 that is axially aligned with lower pinion gear 168 that is axially aligned with upper pinion gear 166. Lower portion 172 of pinion gear 168 extends into opening 174 (FIG. 11) defined by first locking component housing 150 (FIG. 11), thereby fixing the position of pinion gear assembly 164 relative to first locking component housing 150 (FIG. 11), distal bearing 120 (FIG.

11), first locking component 124 and drive gear 86, all of which are shown, in a previous embodiment, in FIG. 11.

Figure 21:
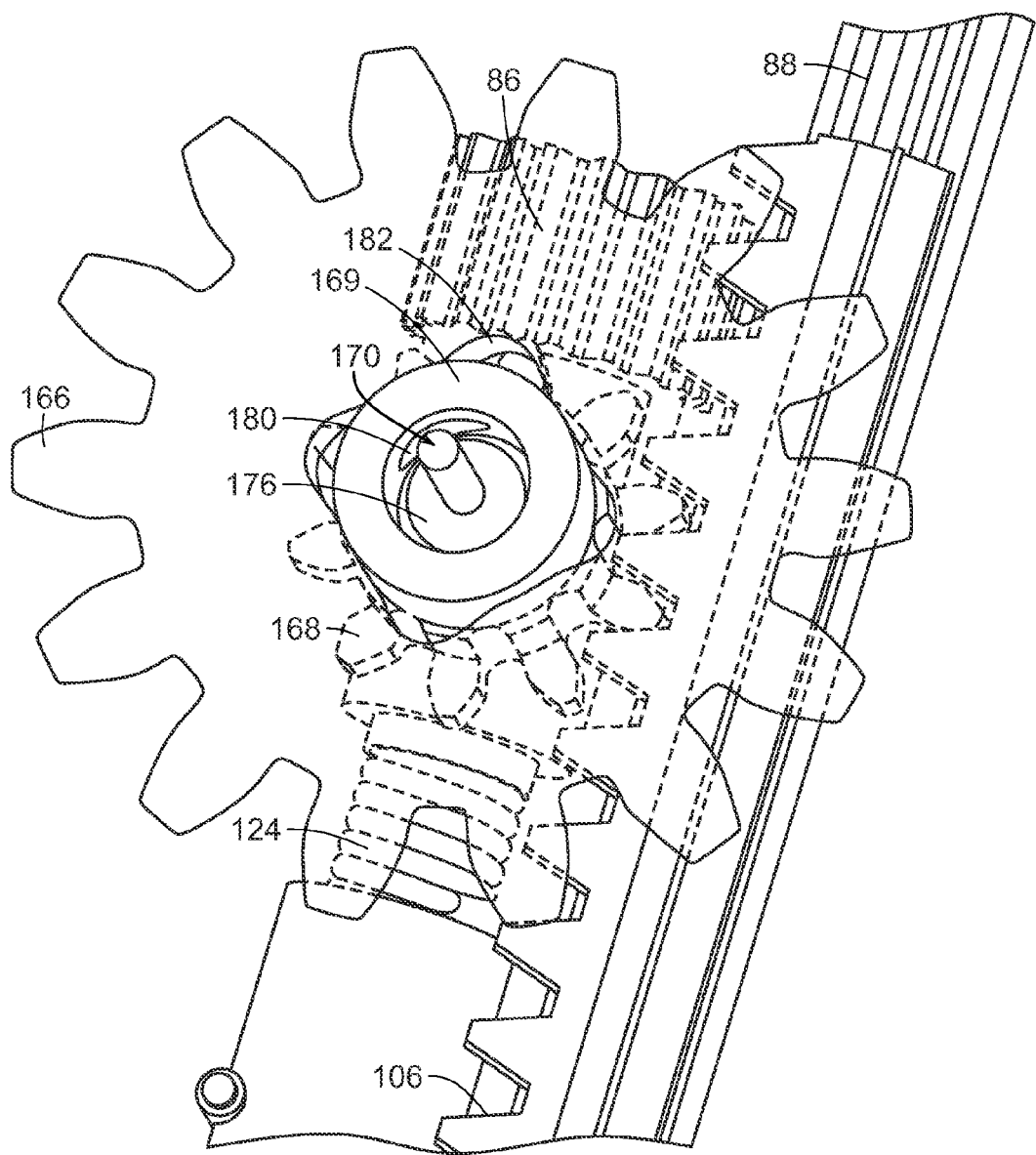
FIG. 21 is a perspective view, partially transparent, of the embodiment of the pinion gear assembly of FIG. 20.
Figure 22:
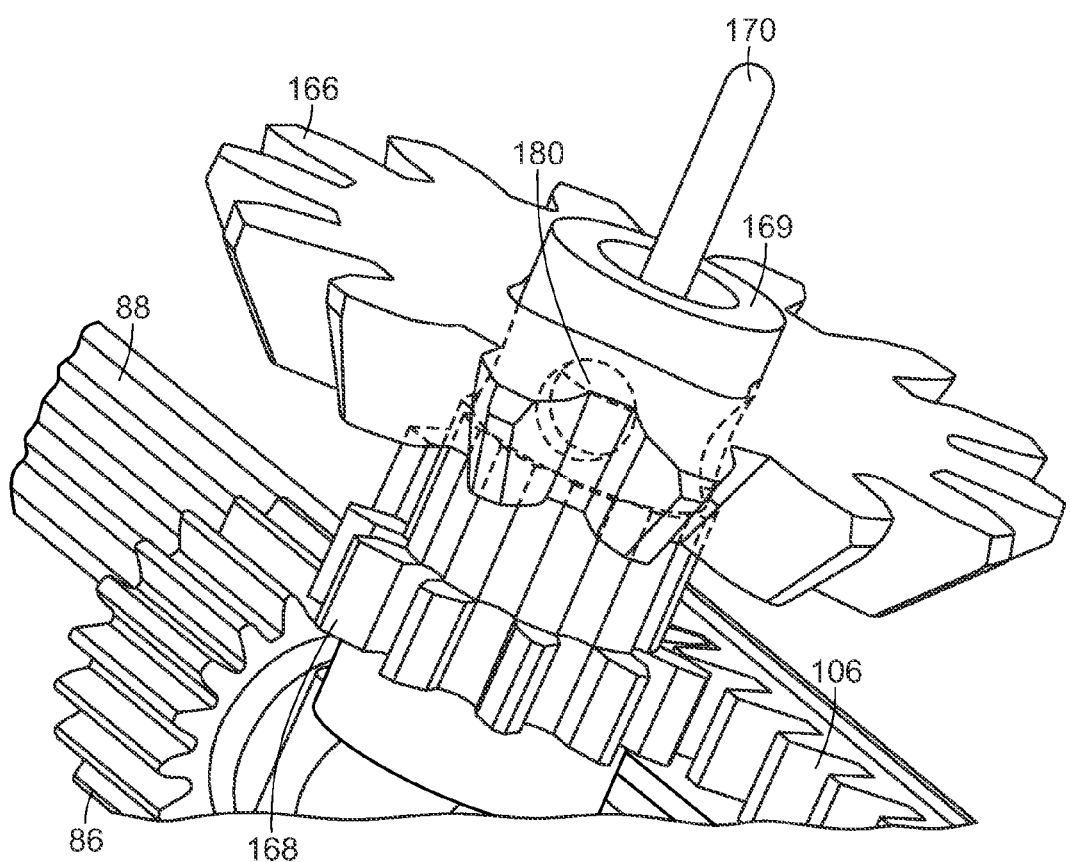
FIG. 22 is another view of the embodiment represented in FIG. 21.
Figure 23:
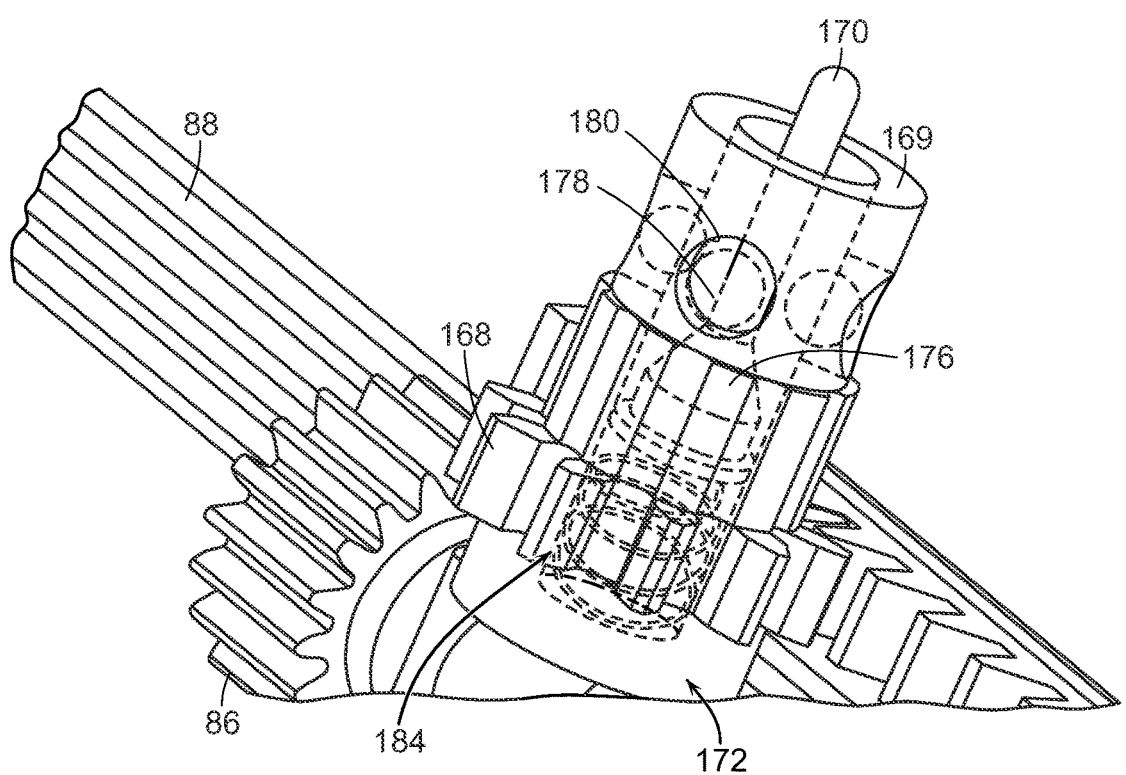
FIG. 23 is a perspective view of the embodiment shown in FIGS. 21 and 22, lacking the upper pinion gear shown in those figures.

FIG. 21 is a perspective view showing engagement of lower pinion gear 168 with gear rack 106 and frustoconical portion 176 of center-pin 170. As can be seen in FIGS. 22 and 23, ball bearings 178 extend through openings 180 defined by pinion gear extension 169 and, when center pin 170 is in an extended position, as shown in FIG. 22, frustoconical portion 176 of center pin 170 forces ball bearings 178 outwardly and into interfering relation with openings 182 (FIG. 21) defined by upper pinion gear 166 (FIGS. 21 and 22) thereby engaging upper pinion gear 166 with lower pinion gear 168. When center pin 170 is actuated by depressing button 82 (FIG. 1), as shown in FIG. 23, ball bearings 178 are forced inward by rotation of upper pinion gear 166 (FIG. 22) relative to lower pinion gear 168 (FIG. 22), whereby upper pinion gear 166 is no longer engaged with lower pinion gear 168. Center-pin 170 is biased in an outward position, whereby upper pinion gear 166 is directed into engagement with lower pinion gear 168 by spring 184 located at the base of center pin 170 (not shown in FIG. 22 or 23).

As can be seen in FIG. 32C, nose cone 50 is fixed to guidewire catheter 12 at a distal end 16 of the guidewire catheter 12. Vascular prosthetic component 58 is disposed within delivery device 10 proximal to nose cone 50 (FIG. 27A).

FIGS. 25 and 26 show perspective and cut-away views, respectively, of the proximal clasp assembly 184 component of the invention. As can be seen in FIG. 25, outer coupling 186 is slideable along proximal end 34 of push rod 32. Fixed component 188 is fixed to the proximal end of the guidewire catheter by pin 192. Outer coupling 186 and fixed component 188 are in mating relation at juncture 190. Spring 194 within outer coupling 186 biases outer coupling 186 against fixed component 188. Proximal clasp assembly 184 is moved from a first position, shown in FIGS. 25, 28B to a second position, shown by applying pressure to tongues 196 on either side of outer coupling 186, and directing outer coupling 186 distally in sufficient degree to allow rotation of outer coupling 186 ninety (90) degrees and then retracting outer coupling 186 so that tongues 196 of outer coupling 186 align between tongues 198 of fixed component 188, as shown in FIG. 32B. Movement of outer coupling 186 from the first position, shown in FIG. 25, to the position shown in FIG. 32B, causes opening of apex clasp assembly 52, whereby proximal capture component is retracted from a first position that is in mating relation to the distal capture component 56 of apex clasp assembly 52 shown in FIG. 31B, to a second position, shown in FIG. 32C, wherein proximal capture component 54 is no longer in mating relation with distal capture component 56. Proximal movement of outer coupling 186 of proximal clasp assembly 184 (FIGS. 25, 28B, 32B) relative to a fixed component 188 to separate proximal capture component 54 (FIG. 31B) from distal capture component 56 (FIGS. 31B, 32C) releases apices 68 of stent 66 at proximal end 60 of vascular prosthetic component 58.

FIGS. 27A-27C are cross sectional views of a portion of delivery device 10 of the invention showing a vascular prosthetic component 58 in an undeployed state within a distal end 202 of delivery device 10. Specifically, as shown in FIG. 27A, vascular prosthetic component 58 is within delivery sheath 200. Distal end 62 of vascular prosthetic component 58 abuts buttress 204. Buttress 204, in turn, is mated to push rod 32 at distal end 206, proximal end 60 of vascular prosthetic component 58 captured at apices 68 of proximal stent 66 with apex clasp assembly 52 when apex clasp assembly 52 is in a closed position, as shown in FIG. 27A. Apex class assembly 52 includes distal capture component 56 at distal end 16 of guidewire catheter 12, and proximal capture component 54 is in mateable relation to distal capture component 56, and attached to distal end 210 of apex release catheter 154. Apex release catheter 154 extends about guidewire catheter 12, and both apex release catheter 154 and guidewire catheter 12 extend through vascular prosthetic component 58 and push rod 32 to proximal clasp assembly 184 (FIG. 26). Delivery sheath 200 is fixed at its proximal end to delivery catheter 28 at distal end 30 and extends about vascular prosthetic component 58 to apex clasp assembly 52, as can be seen in FIG. 27C. Returning to FIG. 27, nose cone 50 is fixed at guidewire catheter 12 distally to distal capture component 56 of apex clasp assembly 52. Outer catheter 48 extends from distal handle nose 44 (FIG. 1), and about delivery catheter 28 and delivery sheath 200, to nose cone 50.

As shown in FIGS. 28A-33B, a method for delivering a vascular prosthesis to a treatment site of the subject employing a delivery device of the invention includes advancing vascular prosthesis 58, while prosthesis 58 is mounted to apex clasp assembly 52 at proximal end 60 of the prosthesis 58. Proximal apex clasp assembly 184 is in a first position shown in FIG. 28B, whereby apex clasp assembly 52 is closed (FIG. 31B). Apices of vascular prosthesis 58 are secured at apex clasp assembly 52 when proximal clasp assembly 184 is in the first position. Apex clasp assembly 52 is, in turn, fixed to distal end 16 of guidewire catheter 12, shifting knob 42 is in a first position when pin 108 is in slot 110 (FIG. 28C), causing push rod 32 to move with longitudinal movement of proximal handle 36. Prosthesis 58 is advanced to a position distal to a vascular treatment site of the subject by rotation of proximal handle 36 in a first direction about handle body 20, having distal end 26, of delivery device 10 through which guidewire catheter 12 extends. Guidewire catheter 12 is disposed within push rod 32 that also extends through handle body 20, wherein guidewire catheter 12 is fixed to push rod 32, such as at a proximal end of guidewire catheter 12 or push rod 32 by pin 192 (FIG. 25), whereby rotation of proximal handle 36 causes longitudinal movement of guidewire catheter 12 and push rod 32 along handle body 20 to thereby at least partially advance prosthesis 58 from outer catheter 48 as can be seen in FIGS. 29A-29B. Optionally, push button 82 of actuator 80 can be depressed to disengage rotation of proximal handle 36 from longitudinal movement of proximal handle 36 along handle body 20, to thereby allow manual advancement of vascular prosthesis 58 to the vascular treatment site of the subject without rotation of proximal handle 36 about handle body 20.

Shifting knob 42 is shifted from a first position, wherein first locking component 124 (FIGS. 10, 11) secures proximal handle 36 to push rod 32, to a second position, whereby first locking component 124 (FIGS. 10, 11) disengages proximal handle 36 from push rod 32 and second locking component 144 (FIGS. 10, 11) engages push rod 32 with handle body 20 at proximal end 24 of handle body 20.

Figure 24:
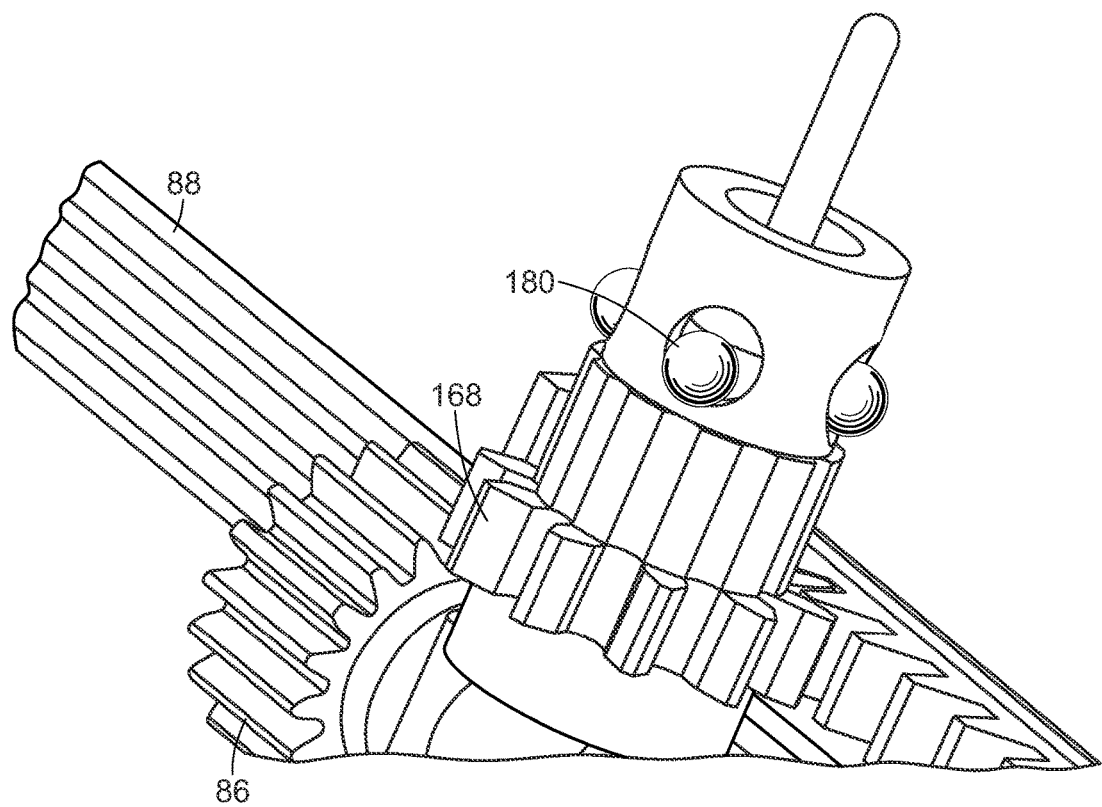
FIG. 24 is another embodiment of the representation shown in FIG. 23.

As can be seen in FIGS. 31A and 31B, proximal handle 36 can then be rotated in a second direction, while actuator push button 82 is not depressed, whereby delivery catheter 28, having a distal end 30 (FIG. 24A) and extending about push rod 32, is withdrawn along push rod 32, and delivery sheath 200 extending from distal end of the delivery catheter (FIGS. 4 through 9) is at least partially retracted from about prosthesis 52. Optionally, push-button 82 of actuator 80 can be depressed, thereby disengaging rotation of proximal handle 36 from handle body 20, to thereby fully retract of delivery sheath 200 from vascular prosthesis 58 without rotation of proximal handle 36 about handle body 20, as can be seen in FIG. 32A.

Proximal clasp assembly 184 is then actuated by compressing outer coupling 186 and moving outer coupling 186 first distally, then rotating outer coupling 186 ninety degrees, and thereafter retracting outer coupling 186 to a second position, shown in FIG. 32B, thereby retracting apex release catheter 154 within push rod 32 (FIGS. 10, 11) and retracting proximal capture component 54 from distal capture component 56. Apices 68 of stent 66 at the proximal end 60 of vascular prosthesis 58 are released from apex clasp assembly 52, and prosthesis 58 is thereby released from the delivery device 10, as can be seen in FIG. 32C. Shifting knob 42 is then moved from the second position to the third position, wherein pin 108 is located in slot 114 between first slot 110 and second slot 112, as can be seen in FIG. 33B, thereby disengaging push rod 32 from handle body 20. Push rod 32 and guidewire catheter 12 are then withdrawn from vascular prosthesis 58 by pulling push rod 32 through handle body 20, thereby completing delivery of vascular prosthesis 58 to the treatment site, as can be seen in FIG. 33A.

While this invention has been particularly shown and described with references to example embodiments thereof, it will be understood by those skilled in the art that various changes in form and details may be made therein without departing from the scope of the invention encompassed by the appended claims The relevant portion of all references cited herein and U.S. Pat. No. 8,070,790 and U.S. patent application Ser. No. 12/459,387 (Publication No. 20100030255) and Ser. No. 12/723,431 (Publication No. 20100234932) are incorporated by reference in their entirety.

What is claimed is:

1. A method for delivering a vascular prosthesis to a treatment site of a subject, comprising the steps of:
   a) advancing the vascular prosthesis, while the vascular prosthesis is mounted at a proximal end of the prosthesis to an apex delivery device that is fixed to a distal end of a guidewire catheter, to a position distal to a vascular treatment site of the subject;
   b) rotating a proximal handle in a first direction about a handle body, having a distal end, of a delivery device through which the guidewire catheter extends, the guidewire catheter disposed within a push rod that also extends through the handle body, wherein the guidewire catheter is fixed to the push rod, whereby rotation of the proximal handle causes longitudinal movement of the guidewire catheter and the push rod along the handle body to thereby at least partially advance the prosthesis to the treatment site, the prosthesis being advanced from within an outer catheter extending from a distal end of the handle body and about the prosthesis;
   c) shifting the position of a first locking component securing the proximal handle to the push rod from a first position to a second position, whereby the first locking component disengages the proximal handle from the push rod and a second locking component engages the push rod with the handle body;
   d) rotating the proximal handle in a second direction, whereby a delivery catheter having a distal end, the delivery catheter extending about the push rod, is withdrawn along the push rod, and a delivery sheath extending from the distal end of the delivery catheter is at least partially retracted from about the prosthesis;
   e) releasing the proximal end of the prosthesis from the apex delivery device;
   f) shifting the second locking component to disengage the push rod from the handle body; and
   g) withdrawing the push rod and the guidewire catheter from within the prosthesis, thereby delivering the vascular prosthesis to the treatment site.

2. The method of claim 1, further including the step of disengaging the proximal handle from the handle body, whereby the proximal handle is slidable along the handle body independently of rotation of the proximal handle.

3. The method of claim 2, wherein the proximal handle is disengaged from the handle body while advancing the prosthesis to the treatment site.

4. The method of claim 3, wherein the proximal handle is disengaged from the handle body while retracting the delivery sheath from about the prosthesis.

5. The method of claim 1, wherein the apex delivery device is an apex clasp assembly, whereby apices of a stent of the prosthesis are held by the apex clasp assembly until released.

6. The method of claim 5, wherein the prosthesis is released from the apex clasp assembly by retracting an apex release catheter extending about the guidewire catheter, the apex release catheter being fixed to a proximal capture component of the apex clasp assembly, whereby the proximal capture component of the apex clasp assembly is separated from a distal capture component of the apex clasp assembly, thereby releasing the apices of the stent of the prosthesis from between the proximal and distal capture components.

7. The method of claim 6, wherein rotation of the proximal handle is disengaged from movement of the proximal handle along the handle body by activating an actuator at the proximal handle.

8. The method of claim 7, wherein shifting the position of the first locking component to disengage the proximal handle from the push rod is obtained by rotating a shifting knob having teeth extending about the handle body from a first position to a second position.

9. The method of claim 8, wherein rotating the shifting knob from the first position to the second position simultaneously causes the second locking component to engage the push rod with the handle body.

10. The method of claim 9, wherein the shifting knob is proximate to or at the distal end of the handle body.

11. The method of claim 10, wherein the shifting knob is linked to the proximal handle by a drive shaft having a proximal end and a distal end, wherein the distal end defines teeth that engage, directly or indirectly, teeth of the shifting knob that defines a row of teeth at the proximal end along a major longitudinal axis of the drive shaft.

12. The method of claim 11, wherein the drive shaft engages a drive gear at the proximal end of the drive shaft, whereby the shifting knob is engaged with the drive gear at all positions of the shifting knob.

13. The method of claim 12, wherein the drive gear is engaged with the drive shaft at all positions of the proximal handle along the handle body.

* * * * *

UNITED STATES PATENT AND TRADEMARK OFFICE
CERTIFICATE OF CORRECTION

PATENT NO. : 9,554,929 B2  
APPLICATION NO. : 14/639280  
DATED : January 31, 2017  
INVENTOR(S) : Samuel Arbefeuille et al.

Page 1 of 1

It is certified that error appears in the above-identified patent and that said Letters Patent is hereby corrected as shown below:

On the Title Page

Item "(72) inventors," add the following fourth inventor:
-- Kory Gunnerson, Cincinnati, OH (US); --

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*